United States Patent
Aggarwal

(10) Patent No.: US 6,686,455 B1
(45) Date of Patent: Feb. 3, 2004

(54) TUMOR NECROSIS FACTOR

(75) Inventor: Bharat B. Aggarwal, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 927 days.

(21) Appl. No.: 08/375,052

(22) Filed: Jan. 18, 1995

Related U.S. Application Data

(63) Continuation of application No. 08/191,751, filed on Feb. 3, 1994, now abandoned, which is a continuation of application No. 07/915,038, filed on Jul. 15, 1992, now abandoned, which is a continuation of application No. 06/677,454, filed on Dec. 3, 1984, now abandoned, which is a continuation-in-part of application No. 06/628,059, filed on Jul. 5, 1984, now abandoned.

(51) Int. Cl.$^7$ .............................. A63J 1/00; C07K 14/00
(52) U.S. Cl. ........................ 530/412; 530/416; 530/422; 530/415; 530/351
(58) Field of Search .............................. 530/351, 350, 530/412, 416, 422, 415; 435/7.1

(56) References Cited

U.S. PATENT DOCUMENTS

| | | | |
|---|---|---|---|
| 4,359,415 A | | 11/1982 | Sloane |
| 4,447,355 A | | 5/1984 | Sakamoto et al. |
| 4,457,916 A | * | 7/1984 | Hayashi et al. ............... 424/95 |
| 4,481,137 A | | 11/1984 | Ohnishi et al. |
| 4,485,038 A | * | 11/1984 | Chadha et al. ................. 435/68 |
| 4,677,063 A | * | 6/1987 | Mark et al. .................. 530/351 |
| 4,677,064 A | * | 6/1987 | Mark et al. .................. 530/351 |
| 4,677,197 A | * | 6/1987 | Lin et al. ..................... 530/416 |
| 4,752,575 A | | 6/1988 | Granger et al. ................ 435/68 |
| 4,758,549 A | | 7/1988 | Mitsuhashi et al. ............ 514/8 |
| 4,870,163 A | * | 9/1989 | Rubin et al. ................. 530/413 |
| 4,871,663 A | * | 10/1989 | Oshima et al. .......... 435/172.3 |
| 4,879,226 A | * | 11/1989 | Wallace et al. .......... 435/240.2 |
| 4,880,915 A | * | 11/1989 | Kajihara et al. ............. 530/415 |
| 5,288,852 A | | 2/1994 | Yamada et al. ............... 530/351 |

FOREIGN PATENT DOCUMENTS

| | | | |
|---|---|---|---|
| DE | 3421731 | 12/1985 | |
| EP | 0090892 | * 4/1982 | |
| EP | 0086475 | 8/1983 | ........... A61K/35/12 |
| EP | 0087087 | 8/1983 | ............ C12N/5/00 |
| EP | 0090892 | 10/1983 | ............ C07G/7/00 |
| EP | 0100641 | 2/1984 | ........... C12P/21/00 |
| EP | 0131789 | 1/1985 | |
| EP | 132125 | 1/1985 | |
| EP | 0134923 | 3/1985 | .......... A61K/35/14 |
| EP | 146026 | 6/1985 | |
| EP | 0148311 | 7/1985 | |
| EP | 0155549 | 9/1985 | |
| EP | 0158286 | 10/1985 | |
| EP | 155549 | 3/1991 | |
| GB | 2094833 | 9/1982 | |
| GB | 2106117 A | 4/1983 | ............ C07G/7/00 |

| | | |
|---|---|---|
| JP | 0186994 | * 10/1984 |

OTHER PUBLICATIONS

Scopes 1982 Protein Purification pp. 139–140. Springer–Verlag New York.*

C.A. No. 184125u vol 93, 1980 Purification and Physic— Chemical Characterization of Rabbit TNF, Ruff et al.*

C.A. No 36 803g vol 101, 1984, Purification of Tumor Generating Factor, Uemura et al.*

Orr et al Lymphokine Res vol 3(4) 1984, Purification and Peptide. . . Lymphoblastoid Cell Line. p. 264.*

Williamson et al, PNAS vol 80, 1983, p. 5397–5401, Humor TNF Produced by B Cell Lines.*

Green et al., "A protein fraction (NHG) from serum of normal humans which is cytotoxic for HELA cells in culture" *Cancer Letters* 11:345–350 (1981).

Helson et al., "Effect of tumor necrosis factor on cultured human melanoma cells" *Nature* 258:731–732 (1975).

Helson et al., "Effects of murine tumor necrosis factor on heterotransplanted human tumors" *Expl. Cell Biol.* 47:53–60 (1979).

Laursen, "Methods in Peptide and Protein Sequence Analysis" *Proceedings of the Third International Conference on Solid Phase Methods in Protein Sequence Analysis* Heidelberg Germany:521–523 (1980).

Olsson et al., "Isolation and Characterization of a T Lymphocyte–Derived Differentiation Inducing fctor for the Myeloid Leukemic Cell Line HL–60" *Blood* 63(3):510–517 (1984).

Orr et al., "Purification and peptide characterization of human α–lymphotoxin obtained from the continuous human lymphoblastoid cell line IR 3.4." *Lymphokine Research* 3(4):264 (1984).

Wanebo et al., "Antitumor Effects of a Normal Human Serum Factor (Normal Human Globulin Fraction 1) on Human Tumor Cells In Vitro" *JNCI* 72(3):545–555 (1984).

Ugelstad et al., "Nature" 303: 95–96 (May 1983).

Rubin et al. "Proc. Natl. Acad. Sci.–USA" 82: 6637–6641 (Oct. 1985).

Matthews et al., "Br. J. Cancer" 38: 302–309 (1978).

Granger et al., "Cell. Immun." 38: 388–402 (1978).

Matthews, "Br. J. Cancer" 40: 534–539 (1979).

Aksamit et al., "J. of Immunology" 122(5): 1785–1790 (May 1979).

(List continued on next page.)

Primary Examiner—Karen Cochrane Carlson
(74) Attorney, Agent, or Firm—Diane L. Marschang

(57) ABSTRACT

A cytotoxic protein designated tumor necrosis factor is identified in nature. It is recovered in substantially homogeneous form by treatment with hydrophobic substances and ion exchange resins. The protein is conclusively identified by its amino acid sequences. Therapeutic compositions are provided.

3 Claims, 11 Drawing Sheets

OTHER PUBLICATIONS

Männel et al., "Infection and Immunity" 30(2): 523–530 (Nov. 1980).
Männel et al., "Infection and Immunity" 28(1): 204–211 (Apr. 1980).
Macfarlan et al., "AJEBAK" 58(P.T. 5) 489–500 (1980).
Ruff et al., "J. of Immunology" 125(4): 1671–1677 (Oct. 1980).
Oettgen et al., "Recent Results Cancer Res" 75: 207–212 (1980).
Matthews et al., "Br. J. Cancer" 42: 416–422 (1980).
Adams et al., "J. of Immunology" 124(1): 293–300 (Jan. 1980).
Granger et al., DeWeck et al., Ed. "Biochemical Characterization of Lymphokines" 279–283 (1980).
Toth et al., "Molecular Immunology" 16: 671–679 (1979).
Ruff + Gifford "Lymphokines" 2: 235–272 (1981).
Kull et al., "J. of Immunology" 126(4): 1279–1283 (Apr. 1981).
Satomi et al., "Japan. J. Exp. Med." 51(6): 317–322 (1981).
Haranaka et al., "Japan. J. Exp. Med." 51(3): 191–194 (1981).
Klostergaard et al., "Molecular Immunology" 18(12): 1049–1054 (1981).
Neumann et al., "Biochem. J." 194: 847–856 (1981).
Matthews, "Immunology" 44: 135–142 (1981).
Granger et al., Mozes et al., Ed. "Cell. Responses to Molecular Modulators" 287–310 (1981).
Kniep et al., "J. of Immunology" 127(2): 417–422 (Aug. 1981).
Hammerstrom "Scand. J. Immunol." 15: 311–318 (1982).
Green et al., "JNCI" 68(6): 997–1003 (Jun. 1982).
Nissen–Meyer et al., "Infection and Immunity" 38(1): 67–73 (Oct. 1982).
Evans, "Cancer Immunol. Immunother." 12: 181–190 (Apr. 1982).
Papermaster et al., Khan et al., Ed. "Human Lymphokines" 459–477 (Pub. Jun. 30, 1982).
Pichyangkul etal., Khan et al., Ed. "Human Lymphokines" 173–183 (Pub. Jun. 30, 1982).
Zacharchuk et al., "P.N.A.S. USA" 80: 6341–6345 (Oct. 1983).
Umeda et al., "Cellular + Molecular Biology" 29(5): 349–352 (1983).
Hall et al., "Cellular Immunology" 76: 58–68 (Apr. 28, 1983).
Wright et al., "J. of Immunology" 130(5): 2479–2483 (May 1983).
Ruddle et al., "Lymphokine Research" 2(1): 23–31 (1983).
Stone–Wolff et al., "J. Exp. Med." 159: 828–843 (Mar. 1984).
Kull et al., "P.N.A.S. USA" 81: 7932–7936 (Dec. 1984).
Buessow et al., "Leukemia Research" 8(5): 801–811 (Oct. 15, 1984).
Powell et al., "Lymphokine Research" 4(1): 13–26 (1985).
Green et al., "J. Natl Cancer Inst." 59(5): 1519–1522 (Nov. 1977).
Gray et al., "Nature" 312: 721–724 (Dec. 20–27, 1984).
Richey "American Laboratory" (Oct., 1982).
Uemura et al., (Translation) "Igaku No Ayumi" 129(4): 237–238 (Apr. 1984).
Rubin et al., "J. Exp. Med." 162: 1099–1104 (Sep. 1985).
Carswell et al., "P.N.A.S. USA" 72(9): 3666–3670 (Sep. 1975).
Trivers et al., "J. of Immunology" 117: 130–135 (Jul. 1976).
Green et al. "P.N.A.S. USA" 73(2): 381–385 (Feb. 1976).
Aggarwal et al. Immunochemistry 102: 130173u (1985).
Aggarwal et al. J. Biol. Chem. 260(4): 2345–2354 (1985).
Pennica et al., Nature 312: 724–729 (Dec. 1984).
Green et al., Cancer Letters 6:235–240 (1979).
Cerletti, N., et al. "Lymphokine Research"6:AB. # 1452 (1987).
Moriya et al. Chem. Abstracts vol. 100 No. 150731 m (1984).
Mitsuhashi et al. Chem. Abstracts VOL 98, No. 204393p (1983).
Fisch et al. Chem. Abstracts vol. 99, No. 137978p (1983).
Armstrong et al., "J.N.C.I." 74(1): 1–9 (Jan. 1985).
Flick et al., "Biological Response Modifiers" P.F. Torrence, Ed. pp. 171–218 (1985).

* cited by examiner

Elution Profile – Controlled Pore Glass

Elution Profile-DEAE

Elution Profile – Chromatofocusing

Combined Activity of Tumor Necrosis Factor and Gamma Interferon

Fig. 10.

Amino Acid and Nucleotide Sequence for Human Tumor Necrosis Factor

```
        -20
     ser pro ser pro gln gln phe pro arg asp leu ile ser pro leu ala gln ala val arg ser ser ser arg thr pro ser
T    TCT CCT TCT CCC CAA CAG TTC CCC AGG GAC CTC ATC AGC CCT CTA GCC CAG GCA GTC AGA TCA TCT TCT CGA ACC CCG AGT 10                                          20                                          30
     asp lys pro val ala his val val ala asn pro gln ala glu gly gln leu gln trp leu asn arg arg ala asn ala leu leu ala asn
     GAC AAG CCT GTA GCC CAT GTT GTA GCA AAC CCT CAA GCT GAG GGG CAG CTC CAG TGG CTG AAC CGC CGG GCC AAT GCC CTC CTG GCC AAT 40                                          50                                          60
     gly val glu leu arg asp asn gln leu val val pro ser glu gly leu tyr leu ile tyr ser gln val leu phe lys gly gln gly cys
     GGC GTG GAG CTG AGA GAT AAC CAG CTG GTG GTG CCA TCA GAG GGC CTG TAC CTC ATC TAC TCC CAG GTC CTC TTC AAG GGC CAA GGC TGC 70                                          80                                          90
     pro ser thr his val leu leu thr his thr ile ser arg ile ala val ser tyr gln thr lys val asn leu leu ser ala ile lys ser
     CCC TCC ACC CAT GTG CTC CTC ACC CAC ACC ATC AGC CGC ATC GCC GTC TCC TAC CAG GTC AAG GTC AAC CTC CTC TCT GCC ATC AAG AGC 100                                         110                                         120
     pro cys gln arg glu thr pro glu gly ala glu ala lys pro trp tyr glu pro ile tyr leu gly gly val phe gln leu glu lys gly
     CCC TGC CAG AGG GAG ACC CCA GAG GGG GCT GAG GCC AAG CCC TGG TAT GAG CCC ATC TAT CTG GGA GGG GTC TTC CAG CTG GAG AAG GGT 130                                         140                                         150                     157
     asp arg leu ser ala glu ile asn arg pro asp tyr leu asp phe ala glu ser gly gln val tyr phe gly ile ile ala leu OP
     GAC CGA CTC AGC GCT GAG ATC AAT CGG CCC GAC TAT CTC GAC TTT GCC GAG TCT GGG CAG GTC TAC TTT GGG ATC ATT GCC CTG TGA GGA GGACGAACATCCAACCTTCCCAAACGCCTCCCCTGCCCCAATCCCCTTCTTATTACCCCTCCTTCAGACACCCTCAACCTCTTCTGGCTCAAAAAGAGAATTGGGGGCTTAGGGTCGGAACC CAAGCTTAGAGAACTTTAAGCAACAAGAACCACCACTTCAGGAATGTGTGGCCTGCACAGTGAAGTGCTGGCAACCACTAAGAATTCAAACTGGGGCCTCCAGAACTCA CTGGGGCCTACAGCTTTGATCCCTGACATCTGGAGAATCTGAGAGACCAGGAGCCTTTGGTTCTGGCCAGAGAATGCTGAGAAGACCTCACCTAGAAATTGACACAAGTGACCT TAGGCCTTCCTCTCCAGATGTTTCCAGACTTCCTTGAGACACGAGCGGGTATCCTGGGGACCCAATGAGGAGCCCAGCTCCTGCCTTGGCTCAGACATGTTTTCCGTGAAAACGAGCTGAACAATAGGCTG TTTATTTATTTACAGATGAATGATATTTATTTGGAGAGACCGGGTATCCTGGGGACCCAATGAGGAGCCCAGCTCCTGCCTTGGCTCAGACATGTTTTCCGTGAAAACGAGCTGAACAATAGGCTG

TTCCCATGTAGCCCCCAGGGAGTTGTGTGTCTGTAATCGCCCTACTATTCAGTGCCGAGAAATAAAGTTTGCTT

CTGCTCCCAGGGAGTTGTGTCTGTAATCGCCCTACTATTCAGTGCCGAGAAATAAAGTTTGCTT
```

TUMOR NECROSIS FACTOR

This application is a continuation application of Ser. No. 08/191,751 filed on Feb. 3, 1994, now abandoned, which is a continuation application of Ser. No. 07/915,038 filed on Jul. 15, 1992, now abandoned, which is a continuation application of Ser. No. 06/677,454 filed on Dec. 3, 1984, now abandoned, which is a continuation-in-part application of Ser. No. 06/628,059 filed on Jul. 5, 1984, now abandoned, which applications are incorporated herein by reference.

This application is a continuation-in-part of U.S. Ser. No. 06/628,059 filed Jul. 5, 1984. Reference is made to U.S. Ser. No. 677,257, now U.S. Pat. No. 4,650,674, and U.S. Ser. No. 881,311, pending.

This application relates to lymphokines. In particular, it relates to cytotoxic factors secreted by lymph cells and methods for making same in recombinant cells.

Immune cells such as B cells, T Cells, natural killer cells and macrophages are known to elaborate substances that exert cytotoxic activity toward tumor cells but which are innocuous to normal cells. These substances have been variously named, for example, lymphotoxin, tumor necrosis factor, NK cell cytotoxic factor, hemorrhagic necrosis factor, macrophage cytotoxin or macrophage cytotoxic factor. At the present time the identities of the proteins associated with these names are unclear. The principal difficulties have been that the biological assays employed to detect the proteins do not discriminate among them, the proteins appear to be found in nature as aggregates or hydrolytic products, and the amounts heretofore obtained have been so small that the high degree of purification needed to fully characterize the proteins has not been reached.

Typically, such cytotoxic substances are found in the sera of intact animals, or in the culture supernatants of lymph cells or cell lines after the animals or cells had been treated with a substance known to stimulate the proliferation of immune cells (an "inducer"). Thereafter the serum or supernatant is recovered and assayed for cytotoxic activity towards a target tumor cell line. A standard target is L-929, a murine tumor cell line. This cell line and others used in bioassays of this type are nonspecific in their lytic response because a variety of apparently discrete lymph cell products are able to effect lysis. Similar nonspecific responses are observed in in vitro tumor necrosis assays. Thus, cytolytic assays which observe for the lysis of cell lines in vitro or tumor necrosis in vivo are inadequate to distinguish among the various cytotoxic lymph products.

Cytotoxic factors tentatively have been classified on the basis of the lymph cells from which they are induced. For example, lymphotoxin is a name commonly applied to the cytotoxic secretory products of B or T lymphocytes, or cell lines derived therefrom, while tumor necrosis factor often is used to describe cytotoxic products of macrophages or their derived cell lines. This classification system, however, has not been developed to the point where there is any assurance that only a single protein is being referred to, or that proteins referred to by different names are in fact different.

Attempts have been made to purify and characterize the cytotoxic factors secreted by each cell type. To the extent that reports vary as to a property of a cytotoxic factor, or are completely inconsistent as to a given property, it could be concluded either that the characterization was erroneous or that a plurality of discrete cytotoxic factors are secreted by each cell type. For example, the cytotoxic products derived from macrophages, monocytes or monocytic cell lines, while sometimes generally referred to as tumor necrosis factor, have been reported to have properties that appear inconsistent with a theory of a single cytotoxic product. See for example the following literature: R. MacFarlan et al., 1980, "AJEBAK" 58(pt 5): 489–500; D. Mannel et al., 1980, "Infection and Immunology" 30(2): 523–530; H. Ohnishi et al., UK patent application 2,106,117A; and J. Hammerstrom, 1982, "Scand J. Immunol." 15: 311–318.

On the other hand C. Zacharchuk et al., 1983, "Proc. Nat. Acad. Sci. USA", 80: 6341–6345 suggest that guinea pig lymphotoxin and a cytotoxic factor from guinea pig macrophages are immunochemically similar, if not identical. Similar conclusions are advanced in Ruff et al., 1981, *Lymphokines* Vol. 2 pp 235–272 at pp 241–242.

The attempts at characterization of immune cytotoxic factors also have focused on using as starting material the sera or peritoneal fluid of animals that have been exposed to immunogenic antigens. These sources contain the entire cornucopia of the stressed immune system, in contrast to the product or products of a single cell type or line. The following should be consulted as examples of publications of this type: S. Green et al., 1982, "J. Nat. Cancer Inst." 68(6): 997–1003 ("tumor necrosis-inducing factor"); M. Ruff et al., 1980, "J. Immunology" 125(4): 1671–1677 ("tumor necrosis factor"); H. Enomoto et al., European Patent Application 86475 ("antitumor substance"); H. Oettgen et al., 1980, "Recent Results Cancer Res." 75: 207–212 ("tumor necrosis factor"); F. Kull et al., 1981, "J. Immunol." 126(4): 1279–1283 ("Tumor Cell Cytotoxin:); D. Mannel et al., 1980, "Infection and Immunity" 28(1): 204–211 ("cytotoxic factor"); N. Matthews et al., 1980, "Br. J. Cancer: 42: 416–422 ("tumor necrosis factor"); S. Green et al., 1976, "Proc. Nat. Acad. Sci. USA:, 73(2): 381–385 ("serum factor"); N. Satomi et al., 1981, "Jpn J. Exp. Med." 51(6): 317–322; N. Matthews, 1979, "Br. J. Cancer" 40: 534–539 ("tumor necrosis factor"); K. Haranaka et al., 1981, "Jpn. J. Exp. Med." 51(3): 191–194 ("tumor necrosis factor"); and L. Old et al., European Patent Application 90892; T. Umeda et al., 1983, "Cellular and Molecular Biology" 29(5): 349–352; H. Enomoto et al., 1983, European Patent Application 86,475.

Further literature which should be consulted is J. Nissen-Meyer et al., 1982, "Infection and Immunity" 38(1): 67–73; J. Klostergaard et al., 1981, "Mol. Immunol." 18(12): 1049–1054; N. Sloane, U.S. Pat. No. 4,359,415; and H. Hayashi et al., U.S. Pat. No. 4,447,355; K. Hanamaka et al., 1983, European Patent Application 90,892; and G. Granger et al., 1978, "Cellular Immunology" 38: 388–402.

European Patent Application Publn. No. 100641 describes a cytotoxic polypeptide which was purified substantially free of impurities from a human lymphoblastoid cell culture. This polypeptide was designated lymphotoxin, although its relationship to other reported cytotoxic polypeptides under the name lymphotoxin is conjectural. It was not known whether this was the sole cytotoxic polypeptide elaborated by immune cells, as suggested by Zacharchuk et al. (Id.), or whether it was one of a potential family of cytotoxic factors.

The polypeptide of the '641 Application has two amino termini, a larger variant ending with Leu Pro Gly Val Gly Leu Thr Pro Ser Ala Ala Gln Thr Ala Arg Gln His Pro Lys Met His Leu Ala His Ser Thr . . . and a smaller variant with the truncated amino terminus His Ser Thr Leu Lys Pro Ala Ala . . . The amino acid sequence of the lymphotoxin of the '641 Application is disclosed in copending U.S. Ser. No. 616,503, filed May 31, 1984, wherein the term "lymphotoxin" is defined.

According to the prior literature the interferons, which exhibit some tumor inhibitory activity, and a poorly characterized protein having an AlaAla amino terminus (U.K. Patent Application Publn. No. 2,117,385A), were candidates for non-lymphotoxin cytotoxic factors. As will be seen, the tumor necrosis factor of this invention is not an interferon, is not lymphotoxin and does not have an AlaAla amino terminus.

It is an object of this invention (a) to conclusively determine whether or not another tumor necrosis factor than lymphotoxin exists and, if so, to identify it in such a way as to clearly distinguish other such factors; (b) to produce such a factor by methods other than induced cell culture, which is expensive and yields product which is contaminated with the inducing agent, or by induction of peripheral blood lymphocytes, which is economically impractical, poorly reproducible, and produces product contaminated with homologous cellular and plasma proteins; (c) to obtain DNA encoding such tumor necrosis factor and to express the DNA in recombinant culture; (d) to synthesize such factor in recombinant culture in the mature form; (e) to modify the coding sequence or structure of such factor; (f) to formulate such factor into therapeutic dosage forms and to administer same to animals for the treatment of tumors; and (g) to produce diagnostic reagents relating to such factor.

SUMMARY

A cytotoxic factor has been purified to homogeneity, characterized and expressed in recombinant culture. This factor is designated tumor necrosis factor (TNF) for convenience and is defined below. It is provided in substantially homogeneous form from cell culture at a specific activity of greater than about 10 million units/mg protein, and ordinarily about 100 million units/mg.

Human tumor necrosis factor synthesized in recombinant culture is characterized by the presence of non-human cell components, including proteins, in amounts and of a character which are physiologically acceptable for administration to patients in concert with the tumor necrosis factor. These components ordinarily will be of yeast, procaryotic or non-human higher eukaryotic origin and present in innocuous contaminant quantities, on the order of less than about 1 percent by weight. Further, recombinant cell culture enables the production of tumor necrosis factor absolutely free of homologous proteins. Homologous proteins are those which are normally associated with the tumor necrosis factor as it is found in nature, e.g. in cells, cell exudates or body fluids. For example, a homologous protein for human tumor necrosis factor is human serum albumin. Heterologous proteins are the converse, i.e. they are not naturally associated or found in combination with the tumor necrosis factor in question.

DNA is provided that encodes tumor necrosis factor and which, when expressed in recombinant or transformed culture, yields copious quantities of tumor necrosis factor. This DNA is novel because cDNA obtained by reverse transcription of mRNA from an induced monocytic cell line contains no introns and is free of any flanking regions encoding other proteins of the organism from which the mRNA originated.

Chromosomal DNA encoding TNF is obtained by probing genomic DNA libraries with cDNA. Chromosomal DNA is free of flanking regions encoding other proteins but may contain introns.

The isolated tumor necrosis factor DNA is readily modified by substitution, deletion or insertion of nucleotides, thereby resulting in novel DNA sequences encoding tumor necrosis factor or its derivatives. These modified sequences are used to produce mutant tumor necrosis factor and to directly express mature tumor necrosis factor. The modified sequences also are useful in enhancing the efficiency of tumor necrosis factor expression in chosen host-vector systems, e.g. by modification to conform to a host cell codon preference.

These novel DNA sequences or fragments thereof are labelled and used in hybridization assays for genetic material encoding tumor necrosis factor.

In processes for the synthesis of tumor necrosis factor, DNA which encodes tumor necrosis factor is ligated into a replicable (reproducible) vector, the vector used to transform host cells, the host cells cultured and tumor necrosis factor recovered from the culture. This general process is used to construct tumor necrosis factor having the characteristics of monocyte tumor necrosis factor or to construct novel derivatives of tumor necrosis factor, depending upon vector construction and the host cell chosen for transformation. The tumor necrosis factor species which are capable of synthesis herein include mature (valyl amino-terminal) tumor necrosis factor, pretumor necrosis factor ("preTNF", defined herein), and derivatives of TNF including (a) fusion proteins wherein TNF or any fragment thereof (including mature tumor necrosis factor) is linked to other proteins or polypeptides by a peptide bond at the amino and/or carboxyl terminal amino acids of TNF or its fragments, (b) TNF fragments, including mature tumor necrosis factor or fragments of preTNF in which any preprotein amino acid is the amino-terminal amino acid of the fragment, (c) mutants of TNF or its fragments (including mature tumor necrosis factor) wherein one or more amino acid residues are substituted, inserted or deleted, and/or (d) methionyl or modified methionyl (such as formyl methionyl or other blocked methionyl species) amino-terminal addition derivatives of the foregoing proteins, fragments or mutants.

Ordinarily, if a mammalian cell is transformed with (a) a vector containing the entire tumor necrosis factor structural gene (including a 5' start codon), or (b) the gene for mature tumor necrosis factor or a tumor necrosis factor derivative operably ligated to a eukaryotic secretory leader (which may also include the tumor necrosis factor secretory leader presequence), and the cell cultured, then mature tumor necrosis factor is recovered from the culture.

Similarly, if DNA which encodes TNF is operably ligated in a vector to a secretory leader which is properly processed by the host cell to be transformed (usually the organism from which the leader sequence was obtained), the host transformed with the vector and cultured, then the tumor necrosis factor is synthesized without amino-terminal methionyl or blocked methionyl. In particular, *E. coli* transformed with vectors in which DNA encoding mature tumor necrosis factor is ligated 5' to DNA encoding the STII enterotoxin signal polypeptide will properly process a high percentage of the hybrid preprotein to mature tumor necrosis factor. Secretory leaders and host cells may be selected that also result in proper transport of mature protein into cell periplasm.

Also within the scope of this invention are derivatives of tumor necrosis factor other than variations in amino acid sequence or glycosylation. Such derivatives are characterized by covalent or aggregative association with chemical moieties. The derivatives generally fall into three classes: salts, side chain and terminal residue covalent modifications, and adsorption complexes.

If DNA encoding mature tumor necrosis factor is operably ligated into a vector, the vector used to transform a host cell and the cell cultured, mature tumor necrosis factor is found in the cell cytoplasm. Accordingly, it is unnecessary to devise secretion systems in order to obtain mature tumor necrosis factor. This was surprising because, ordinarily, direct expression yields methionylated protein. Further, the protein is stable and soluble in recombinant cell culture, i.e., it is neither proteolytically cleaved by intracellular proteases nor deposited as refractile bodies. Accordingly, novel fermentations are provided that comprise lower eukaryotic or prokaryotic cells having unmethionylated mature tumor necrosis factor located within the cytoplasm of such cells.

While tumor necrosis factor may be prepared by culturing animal cell lines, e.g. a monocytic cell line induced by growth in the presence of 4-beta-phorbol-12-myristate-13-acetate (PMA) or immortal cell lines such as hybridomas or EBV transformed cells (U.S. Pat. No. 4,464,465), it is preferable to synthesize tumor necrosis factor in recombinant cell culture as described further below.

Once tumor necrosis factor is prepared by fermentation it generally is purified by recovering the supernatant culture fluid or lysed cell culture, removing solids, adsorbing tumor necrosis factor from the supernatant admixture, (containing tumor necrosis factor and other proteins) onto a hydrophobic substance, eluting tumor necrosis factor from the substance, adsorbing tumor necrosis factor onto a tertiary amino anion exchange resin, eluting tumor necrosis factor from the resin, adsorbing tumor necrosis factor onto an anion exchange resin (preferably quaternary amino-substituted) having substantially uniform particle size, and eluting tumor necrosis factor from the resin. Optionally, the tumor necrosis factor compositions are concentrated and purified by chromatofocusing at any point in the purification procedure, for example by isoelectric focusing or passage through a sieving gel such as Sephadex G-25.

The purified tumor necrosis factor from recombinant or induced cell culture is combined for therapeutic use with physiologically innocuous stabilizers and excipients and prepared in dosage form as by lyophilization in dosage vials or storage in stabilized aqueous preparations. Alternatively, tumor necrosis factor is incorporated into a polymer matrix for implantation into tumors or surgical sites from which tumors have been excised, thereby effecting a timed-release of the tumor necrosis factor in a localized high gradient concentration.

The compositions herein are obtained free of contaminant cytotoxic factors such as lymphotoxin, interferons or other cytotoxic proteins referred to in the literature. However, in therapeutic applications tumor necrosis factor is advantageously combined with predetermined amounts of lymphotoxin and/or interferon. Compositions containing tumor necrosis factor and an interferon such as gamma interferon are particularly useful since they have been found to exert a synergistic cytotoxic activity.

Tumor necrosis factor compositions are administered to animals, particularly patients bearing malignant tumors, in therapeutically effective doses. Suitable dosages will be apparent to the artisan in the therapeutic context, as is further described infra.

BRIEF DESCRIPTION OF THE DRAWINGS

FIG. 10 sets forth the nucleotide and amino acid sequence for mature human tumor necrosis factor and a portion of the tumor necrosis factor secretory leader.

DETAILED DESCRIPTION

Figure 1:
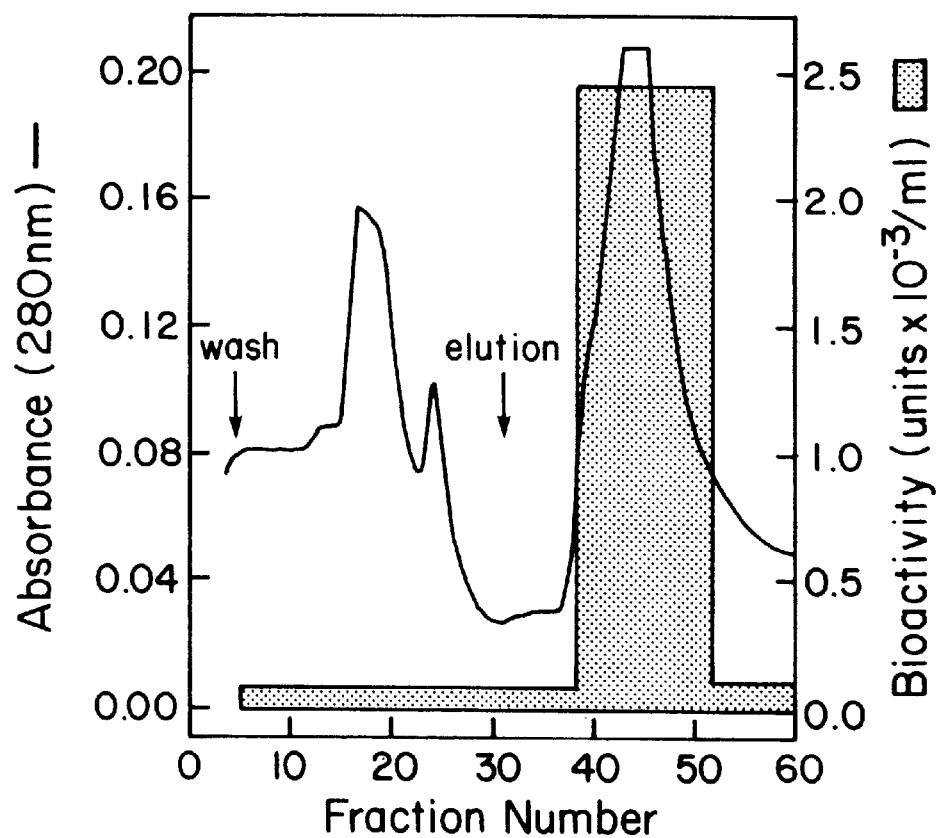
FIG. 1 shows the elution profile of tumor necrosis factor from controlled pore glass.

Tumor necrosis factor is defined for the purposes herein as a polypeptide other than lymphotoxin capable of preferential cytotoxic activity and having a region showing functional amino acid homology with the mature tumor necrosis factor amino acid sequence set forth in FIG. 10, a fragment thereof, or a derivative of such polypeptide or fragment.

Preferential cytotoxic activity is defined as the preferential destruction or growth inhibition of tumor cells when compared to normal cells under the same conditions. Preferential cytotoxic activity is detected by the effect of the polypeptide on tumor cells in vivo or in vitro as compared with normal cells or tissue. Cell lysis is generally the diagnostic indicia in vitro, while tumor necrosis is determined in in vivo experiments. However, cytotoxic activity may be manifest as cytostasis or antiproliferative activity. Suitable assay systems are well known. For example, the cell-lytic assay used to determine the specific activity of tumor necrosis factor described below is acceptable, as is the assay described in B. Aggarwal et al., in "Thymic Hormones and Lymphokines", 1983, ed. A. Goldstein, Spring Symposium on Health Sciences, George Washington University Medical Center (the A549 cell line referred to in this literature is available from the ATCC as CCL185).

The specific activity of TNF is cast in terms of target cell lysis, rather than cytostasis. One unit of tumor necrosis factor is defined as the amount required for 50 percent lysis of the target cells plated in each well in accord with Example 1. However, this is not meant to exclude other assays for measuring specific activity, e.g. methods based on target cell growth rate.

PreTNF is a species of tumor necrosis factor included within the foregoing definition of tumor necrosis factor. It is characterized by the presence in the molecule of a signal (or leader) polypeptide which serves to post-translationally direct the protein to a site inside or outside of the cell. Generally, the signal polypeptide (which will not have tumor necrotic activity in its own right) is proteolytically cleaved from a residual protein having tumor necrosis factor activity as part of the secretory process in which the protein is transported into the host cell periplasm or culture medium. The signal peptide may be microbial or mammalian (including the native, 76 residue presequence), but it preferably is a signal which is homologous to the host cell.

Native tumor necrosis factor from normal biological sources has a calculated molecular weight of about 17,000 on sodium dodecyl sulfate polyacrylamide gel electrophoresis (SDS-PAGE) as described infra, an isoelectric point of about 5.3, and susceptibility to trypsin hydrolysis at multiple sites. Native tumor necrosis factor which has been purified by reverse phase HPLC is trypsin hydrolyzed into at least nine fragments under the conditions described infra. The precise number of fragments into which tumor necrosis factor is hydrolyzed by trypsin will depend upon such factors as trypsin activity, tumor necrosis factor concentration and incubation parameters, including the ionic strength, pH, temperature and time of incubation.

Tumor necrosis factor does not appear to be a glycoprotein, as it is not retained on lectin affinity columns and analysis of the deduced amino acid sequence contains no likely glycosylation sites. Also, material produced in recombinant E. coli culture (which does not have the ability to glycosylate) co-migrates with natural TNF on SDS-PAGE.

The degree of amino acid sequence homology which brings a polypeptide within the scope of the definition of tumor necrosis factor herein will vary depending upon whether the homology between the candidate protein and tumor necrosis factor falls within or without the tumor necrosis factor regions responsible for cytotoxic activity; domains which are critical for cytotoxic activity should exhibit a high degree of homology in order to fall within the definition, while sequences not involved in maintaining tumor necrosis factor conformation or in effecting receptor binding may show comparatively low homology. In addition, critical domains may exhibit cytolytic activity and yet remain homologous as defined herein if residues containing functionally similar amino acid side chains are substituted. Functionally similar refers to dominant characteristics of the side chains such as basic, neutral or acid, or the presence or absence of steric bulk. However, tumor necrosis factor as defined herein specifically excludes any proteins identified as lymphotoxin in copending U.S. Ser. No. 616,503, incorporated herein by reference.

Generally a polypeptide defined as tumor necrosis factor will contain regions substantially homologous with the FIG. 10 protein or fragments thereof over a continuous block of about from 20 to 100 amino acid residues in particular the blocks encompassed by residues 35–66 and 110–133.

A most significant factor in establishing the identity of a polypeptide as tumor necrosis factor is the ability of antisera which are capable of substantially neutralizing the cytolytic activity of mature tumor necrosis factor as set forth in FIG. 10 to also substantially neutralize the cytolytic activity of the polypeptide in question. However it will be recognized that immunological identity and cytotoxic identity are not necessarily coextensive. A neutralizing antibody for the tumor necrosis factor of FIG. 10 may not bind a candidate protein because the neutralizing antibody happens to not be directed to specifically bind a site on tumor necrosis factor that is critical to its cytotoxic activity. Instead, the antibody may bind an innocuous region and exert its neutralizing effect by steric hinderance. Therefore a candidate protein mutated in this innocuous region might no longer bind the neutralizing antibody, but it would nonetheless be tumor necrosis factor in terms of substantial homology and biological activity.

It is important to observe that characteristics such as molecular weight, isoelectric point and the like for the native or wild type mature human tumor necrosis factor of FIG. 10 obtained from peripheral lymphocyte or established cell line cultures are descriptive only for the native species of tumor necrosis factor. Tumor necrosis factor as contemplated by the foregoing definition will include other species which will not exhibit all of the characteristics of native tumor necrosis factor. While tumor necrosis factor as defined herein includes native tumor necrosis factor, other related cytotoxic polypeptides will fall within the definition. For example, TNF derivatives like the insertion mutants, deletion mutants, or fusion proteins described above will bring tumor necrosis factor outside of the molecular weight established for native human tumor necrosis factor (fusion proteins with mature tumor necrosis factor or preTNF itself as well as insertion mutants will have a greater molecular weight than native, mature tumor necrosis factor, while deletion mutants of native, mature tumor necrosis factor will have a lower molecular weight). Similarly, tumor necrosis factor may be engineered in order to reduce or eliminate susceptibility to hydrolysis by trypsin or other proteases. Finally, post-translational processing of human preTNF in cell lines derived from nonprimate mammals may produce microheterogeneity in the amino terminal region, so that valine will no longer be the amino terminal amino acid.

The amino acid sequence for human tumor necrosis factor deduced from its cDNA is described in FIG. 10. Mature or native tumor necrosis factor is represented by amino acid residues 1 to 157. A 76 residue signal sequence is believed to be removed during normal processing of the translated transcript to produce the mature protein. Trypsin hydrolysis sites are denoted by arrows.

Note that the language "capable" of cytotoxic activity or in vivo tumor necrosis means that the term tumor necrosis factor includes polypeptides which can be converted, as by enzymatic hydrolysis, from an inactive state analogous to a zymogen to a polypeptide fragment which exhibits the desired biological activity. Typically, inactive precursors will be fusion proteins in which mature tumor necrosis factor is linked by a peptide bond at its carboxyl terminus to a human protein or fragment thereof. The sequence at this peptide bond or nearby is selected so as to be susceptible to proteolytic hydrolysis to release tumor necrosis factor, either in vivo or, as part of a manufacturing protocol, in vitro. The tumor necrosis factor that is so generated then will exhibit the definitionally-required cytotoxic activity.

While tumor necrosis factor ordinarily is meant to mean human tumor necrosis factor, tumor necrosis factor from sources such as murine, porcine, equine or bovine is included within the definition of tumor necrosis factor so long as it otherwise meets the standards described above for homologous regions and cytotoxic activity. TNF is not species specific, e.g., human TNF is active on mouse tumors. Therefore, TNF from one species can be used in therapy of another.

Tumor necrosis factor also includes multimeric forms. Tumor necrosis factor spontaneously aggregates into multimers, usually dimers or higher multimers. Multimers are cytotoxic and accordingly are suitable for use in in vivo therapy. While it is desirable to express and recover tumor necrosis factor as a substantially homogeneous multimer or monomer, tumor necrosis factor may be used therapeutically as a mixture of different multimers.

Derivatives of tumor necrosis factor are included within the scope of the term tumor necrosis factor. Derivatives include amino acid sequence mutants, glycosylation variants and covalent or aggregative conjugates with other chemical moieties. Covalent derivatives are prepared by linkage of functionalities to groups which are found in the TNF amino acid side chains or at the N- or C-termini, by means known in the art. These derivatives may, for example, include: aliphatic esters or amides of the carboxyl terminus or residues containing carboxyl side chains, e.g., asp10; O-acyl derivatives of hydroxyl group-containing residues such as ser52, ser3, ser4 or ser5; N-acyl derivatives of the amino terminal amino acid or amino-group containing residues, e.g. lysine or arginine; and derivatives of cys101 and cys69. The acyl group is selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups. Preferred derivatization sites are at cysteine and histidine residues.

Covalent or aggregative derivatives are useful as reagents in immunoassay or for affinity purification procedures. For example, tumor necrosis factor is insolubilized by covalent bonding to cyanogen bromide-activated Sepharose by methods known per se or adsorbed to polyolefin surfaces (with or without glutaraldehyde cross-linking) for use in the assay or purification of anti-TNF antibodies or cell surface receptors. Tumor necrosis factor also is labelled with a detectable group, e.g., radioiodinated by the chloramine T procedure, covalently bound to rare earth chelates or conjugated to another fluorescent moiety for use in diagnostic assays, especially for diagnosis of TNF levels in biological samples by competitive-type immunoassays. Such derivatives may fall outside of the TNF definition above because it is not necessary that they show cytotoxic activity, only cross-reactivity with anti-TNF.

Mutant tumor necrosis factor derivatives include the predetermined, i.e. site specific, mutations of TNF or its fragments. The objective of mutagenesis is to construct DNA that encodes tumor necrosis factor as defined above, i.e., tumor necrosis factor which exhibits cytotoxic activity towards tumor cells in vitro or causes tumor necrosis in vivo, and which retains residual homology with the FIG. 10 sequence, but which also exhibits improved properties and activity. Mutant tumor necrosis factor is defined as a polypeptide otherwise falling within the homology definition for tumor necrosis factor set forth herein but which has an amino acid sequence different from that of tumor necrosis factor whether by way of deletion, substitution or insertion. For example, the lysine or arginine residues of tumor necrosis factor (arginine 2, 6, 82, 44 and 131 and lysine 98, 90, and 65,) may be mutated to histidine or another amino acid residue which does not render the protein proteolytically labile. Similarly, cysteine 101 could be replaced by other residues and cross-linked chemically in order to confer oxidative stability. It is not necessary that mutants meet the activity requirements for tumor necrosis factor, for even biologically inactive mutants will be useful upon labelling or immobilization as reagents in immunoassays. However, in this case the mutants will retain at least one epitopic site which is cross-reactive with antibody to tumor necrosis factor.

The regions of the tumor necrosis molecule within residues 35 to 66 and 110 to 133 inclusive show substantial homology (50 percent) with lymphotoxin. The hydrophobic carboxy-termini (tumor necrosis factor residues 150 to 157) of the two molecules also are significantly conserved. Since both proteins demonstrate cytotoxic activity or in vivo tumor necrosis these regions are believed to be important in the shared activity of lymphotoxin and tumor necrosis factor. As such, the residues in these regions are preferred for mutagenesis having the objective of directly affecting the activity of tumor necrosis factor on a given cell. The relatively unconserved region at tumor necrosis factor residues 67–109 may function to correctly position the two surrounding relatively homologous regions in a conformation essential for cytotoxic activity. Such positioning, which could be achieved by a Cys69–Cys101 disulfide bond in tumor necrosis factor, might be similarly accomplished by the corresponding region of lymphotoxin and could account for differences in specificity and activity between the two molecules. In this connection, since these residues are postulated to represent the active core of tumor necrosis factor they may be synthesized chemically or by deletion mutagenesis as truncated, short-length polypeptides having tumor necrosis factor activity.

While the mutation site is predetermined, it is unnecessary that the mutation per se be predetermined. For example, in order to optimize the performance of the position 131 mutants random mutagenesis may be conducted at the codon for arginine 131 and the expressed tumor necrosis factor mutants screened for the optimal combination of cytotoxic activity and protease resistance. Techniques for making substitution mutations at predetermined sites in DNA having a known sequence is well known, for example M13 primer mutagenesis.

Tumor necrosis factor mutagenesis is conducted by making amino acid insertions, usually on the order of about from 1 to 10 amino acid residues, or deletions of about from 1 to 30 residues. Substitutions, deletions, insertions or any subcombination may be combined to arrive at a final construct. Insertions include amino or carboxyl-terminal fusions, e.g. a hydrophobic extension added to the carboxyl terminus. Preferably, however, only substitution mutagenesis is conducted. Obviously, the mutations in the encoding DNA must not place the sequence out of reading frame and preferably will not create complementary regions that could produce secondary mRNA structure.

Not all mutations in the DNA which encode the tumor necrosis factor will be expressed in the final secreted product. For example, a major class of DNA substitution mutations are those in which a different secretory leader or signal has been substituted for the native human secretory leader, either by deletions within the leader sequence or by substitutions, wherein most or all of the native leader is exchanged for a leader more likely to be recognized by the intended host. For example, in constructing a procaryotic expression vector the human secretory leader is deleted in favor of the bacterial alkaline phosphatase or heat stable enterotoxin II leaders, and for yeast the leader is substituted in favor of the yeast invertase, alpha factor or acid phosphatase leaders. However, the human secretory leader may be recognized by hosts other than human cell lines, most likely in cell culture of higher eukaryotic cells. When the secretory leader is "recognized" by the host, the fusion protein consisting of tumor necrosis factor and the leader ordinarily is cleaved at the leader-tumor necrosis factor peptide bond in the events that lead to secretion of the tumor necrosis factor. Thus, even though a mutant preTNF DNA is used to transform the host, and mutant preTNF is synthesized as intermediate, the resulting tumor necrosis factor ordinarily is native, mature tumor necrosis factor.

Another major class of DNA mutants that are not expressed as tumor necrosis factor derivatives are nucleotide substitutions made to enhance expression, primarily to avoid amino terminal loops in the transcribed mRNA (see copending U.S. Ser. No. 303,687, incorporated by reference) or to provide codons that are more readily transcribed by the selected host, e.g. the well-known *E. coli* preference codons for *E. coli* expression.

Substantially homogeneous tumor necrosis factor means tumor necrosis factor which is substantially free of other proteins native to the source from which the tumor necrosis factor was isolated. This means that homogeneous tumor necrosis factor is substantially free of blood plasma proteins such as albumin, fibrinogen, serine proteases, α-globulins, non-tumor necrosis factor cytotoxic polypeptides such as lymphotoxin or interferons, or other proteins of the cell or organism which serves as the synthetic origin of the tumor necrosis factor, including whole cells and particulate cell debris. However, homogeneous tumor necrosis factor may include such substances as the stabilizers and excipients described below, predetermined amounts of proteins from the cell or organism that serves as the synthetic origin, proteins from other than the tumor necrosis factor source cells or organisms, and synthetic polypeptides such as poly-L-lysine. Recombinant tumor necrosis factor which is expressed in an allogeneic, e.g. bacterial, host cell of course will be expressed completely free of gene source proteins.

Tumor necrosis factor is preferably synthesized in cultures of recombinant organisms. Neither peripheral blood lymphocytes (PBLs) nor cell lines are desirable. It is difficult in practice to obtain PBLs of one class which are free of contamination by cells of other classes, e.g. to obtain macrophages free of B or T cells. Such contamination will render the separation procedure applied to the products of such cells more difficult because of other potential cytotoxic factors and proteins released by the contaminant cells. Furthermore, tumor necrosis factor obtained from nonrecombinant culture is expensive and will consist solely of native tumor necrosis factor, such cultures thereby lacking in the flexibility of recombinant culture to improve upon the characteristics of tumor necrosis factor.

DNA which encodes tumor necrosis factor is obtained by chemical synthesis, by screening reverse transcripts of mRNA from PBL or cell line cultures, or by screening genomic libraries from any cell. Suitable cell line cultures comprise monocytic cell lines such as promyelocytic cell lines designated "HL-60" in the art (one of which is available from the ATCC as CCL 240) or the histiocytic lymphoma cell line U 937 (ATCC CRL 1593). These and other cell lines are induced to express and secrete tumor necrosis factor by exposure of the cells to chemical or physical agents known in the art, generally tumorigenic or mitogenic agents. Tumor necrosis factor can be induced effectively in certain monocytic cell lines only with PMA; otherwise conventional agents such lipopolysaccharide, staphylococcal enterotoxin B, or thymosin α-1 were not as effective as PMA at inducing tumor necrosis factor in these cell lines. Since a variable amount of screening is required to locate a cell line expressing tumor necrosis factor (and therefore containing the desired mRNA) it may be more efficient to simply synthesize the gene. Synthesis is advantageous because unique restriction sites can be introduced (thereby facilitating the use of the gene in vectors containing restriction sites otherwise present in the native sequence) and steps can be taken to enhance translational efficiency, as discussed below.

This DNA is covalently labelled with a detectable substance such as a fluorescent group, a radioactive atom or a chemiluminescent group by methods known per se. It is then used in conventional hybridization assays. Such assays are employed in identifying TNF vectors and transformants as described in the Examples infra, or for in vitro diagnosis such as detection of TNF mRNA in blood cells.

The mRNA for TNF, surprisingly, is relatively rare even in induced HL-60 cells, perhaps due to instability in the messenger resulting from unknown causes. Furthermore, the time course of appearance of TNF mRNA after cell induction is important. TNF mRNA appears in the cells for only a brief period at about 4 hours post-induction. In this respect its appearance is distinct from that of lymphotoxin, which appears at about 12 hours post-induction. This makes the cDNA easy to overlook were one not apprised as to what to look for. However, once its presence is appreciated and completely complementary DNA made available, as is enabled by the disclosures herein, it is routine to screen cDNA libraries of induced HL-60 or PBLs for tumor necrosis factor cDNA using probes having sequences of such DNA. The two HL-60 phage libraries screened in the Examples contain a relatively consistent number of positive plaques, so it is clear that routine hybridization assays will identify phage containing the desired cDNA.

Tumor necrosis factor-synthesizing cells of an HL-60 cell line initially are cultured in conventional fashion until reaching a density of about $8-12\times10^5$ cells/ml. The cells are removed from the culture, washed, transferred to serum-free medium and grown in medium containing PMA. The culture then is continued until the desired concentration of tumor necrosis factor has accumulated in the culture medium, ordinarily about 400 tumor necrosis factor units/ml. Thereafter the culture supernatant is preferably clarified by centrifugation or other means of separating cell debris from the soluble components. Centrifugation should be carried out at low speed so as to remove only suspended particles. The supernatant is then purified as described infra.

Alternatively, and preferably, tumor necrosis factor is synthesized in host cells transformed with vectors containing DNA encoding tumor necrosis factor. A vector is a replicable DNA construct. Vectors are used herein either to amplify DNA encoding tumor necrosis factor and/or to express DNA which encodes tumor necrosis factor. An expression vector is a replicable DNA construct in which a DNA sequence encoding tumor necrosis factor is operably linked to suitable control sequences capable of effecting the expression of tumor necrosis factor in a suitable host. Such control sequences include a transcriptional promoter, an optional operator sequence to control transcription, a sequence encoding suitable mRNA ribosomal binding sites, and sequences which control termination of transcription and translation.

Vectors comprise plasmids, viruses (including phage), and integratable DNA fragments (i.e., integratable into the host genome by recombination). Once it has transformed a suitable host, the vector replicates and functions independently of the host genome, or may, in some instances, integrate into the genome itself. In the present specification, "vector" is generic to "plasmid", but plasmids are the most commonly used form of vector at present. However, all other forms of vectors which serve an equivalent function and which are, or become, known in the art are suitable for use herein. Suitable vectors will contain replicon and control sequences which are derived from species compatible with the intended expression host. Transformed host cells are cells which have been transformed or transfected with tumor necrosis factor vectors constructed using recombinant DNA techniques. Transformed host cells ordinarily express tumor necrosis factor. The expressed tumor necrosis factor will be deposited intracellularly or secreted into either the periplasmic space or the culture supernatant, depending upon the host cell selected.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Suitable host cells are prokaryotes, yeast or higher eukaryotic cells. Prokaryotes include gram negative or gram positive organisms, for example *E. coli* or Bacilli. Higher eukaryotic cells include established cell lines of mammalian origin as described below. A preferred host cell is the phage resistant *E. coli* W3110 (ATCC 27,325) strain described in the Examples, although other prokaryotes such as *E. coli* B, *E. coli* X1776 (ATCC 31,537), *E. coli* 294 (ATCC 31,446), pseudomonas species, or *Serratia Marcesans* are suitable.

Prokaryotic host-vector systems are preferred for the expression of tumor necrosis factor. While the tumor necrosis factor molecule contains two cysteine residues, thereby implying a modest potential requirement for post-translational processing to form a potential disulfide bond, *E. coli* for example expresses biologically active tumor necrosis factor. A plethora of suitable microbial vectors are available. Generally, a microbial vector will contain an origin of replication recognized by the intended host, a promoter which will function in the host and a phenotypic selection gene, for example a gene encoding proteins conferring antibiotic resistance or supplying an auxotrophic requirement. Similar constructs will be manufactured for other hosts. *E. coli* is typically transformed using pBR322, a plasmid derived from an *E. coli* species (Bolivar, et al., 1977, "Gene" 2: 95). pBR322 contains genes for ampicillin and tetracycline resistance and thus provides easy means for identifying transformed cells.

Vectors must contain a promoter which is recognized by the host organism. This is generally a promoter homologous to the intended host. Promoters most commonly used in recombinant DNA construction include the β-lactamase (penicillinase) and lactose promoter systems (Chang et al., 1978, "Nature", 275: 615; and Goeddel et al., 1979, "Nature" 281: 544), a tryptophan (trp) promoter system (Goeddel et al., 1980, "Nucleic Acids Res." 8: 4057 and EPO App. Publ. No. 36,776) and the tac promoter [H. De Boer et al., "Proc. Nat'l. Acad. Sci. U.S.A." 80: 21–25 (1983)]. While these are the most commonly used, other known microbial promoters are suitable. Details concerning their nucleotide sequences have been published, enabling a skilled worker operably to ligate them to DNA encoding tumor necrosis factor in plasmid vectors (Siebenlist et al., 1980, "Cell" 20: 269) and the DNA encoding tumor necrosis factor. At the present time the preferred vector is a pBR322 derivative containing the *E. coli* alkaline phosphatase promoter with the trp Shine-Dalgarno sequence. The promoter and Shine-Dalgarno sequence are operably linked to the DNA encoding the TNF, i.e., they are positioned so as to promote transcription of TNF mRNA from the DNA.

In addition to prokaryates, eukaryotic microbes such as yeast cultures are transformed with tumor necrosis factor-encoding vectors. *Saccharomyces cerevisiae*, or common baker's yeast is the most commonly used among lower eukaryotic host microorganisms, although a number of other strains are commonly available. Yeast vectors generally will contain an origin of replication from the 2 micron yeast plasmid or an autonomously replicating sequence (ARS), a promoter, TNF, sequences for polyadenylation and transcription termination and a selection gene. A suitable plasmid for tumor necrosis factor expression in yeast is YRp7, (Stinchcomb et al., 1979, "Nature", 282: 39; Kingsman et al., 1979, "Gene", 7: 141; Tschemper et al., 1980, "Gene", 10: 157). This plasmid already contains the trp1 gene which provides a selection marker for a mutant strain of yeast lacking the ability to grow in tryptophan, for example ATCC No. 44076 or. PEP4-1 (Jones, 1977, "Genetics", 85,: 12). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland et al., 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the tumor necrosis factor coding sequences to provide polyadenylation of the mRNA and termination.

In addition to microorganisms, cultures of cells derived from multicellular organisms may also be used as hosts. This, however; is not preferred because of the excellent results obtained thus far with TNF expressing microbes. In principal, any higher eukaryotic cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication (Fiers et al., 1978, "Nature", 273: 113). Smaller or larger SV40 fragments may also be used, provided the approximately 250 bp sequence extending from the Hind III site toward the Bgl I site located in the viral origin of replication is included. Further, it is also possible, and often desirable, to utilize human genomic promoter, control and/or signal sequences normally associated with tumor necrosis factor, provided such control sequences are compatible with the host cell systems.

An origin of replication may be provided either by construction of the vector to include an exogenous origin, such as may be derived from SV40 or other viral (e.g. Polyoma, Adenovirus, VSV, or BPV) source, or may be provided by the host cell chromosomal replication mechanism. If the vector is integrated into the host cell chromosome, the latter is often sufficient.

In selecting a preferred host mammalian cell for transfection by vectors which comprise DNA sequences encoding both tumor necrosis factor and dihydrofolate reductase (DHFR), it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Natl. Acad. Sci." (USA) 77: 4216.

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-K1 (ATCC No. CCL 61).

Tumor necrosis factor initially is recovered from cultures. Transformed nonsecreting cells are lysed by sonication or other acceptable method and debris separated by centrifugation, while the supernatants from secreting cells (such as induced cell lines) are simply separated from the cells by centrifugation. Then any one or more of the following steps may be used, or other methods entirely may be substituted. The following method was used to purify tumor necrosis factor to a degree sufficient for sequencing. This is not necessarily coextensive with the purification required for a therapeutic product.

As an initial purification step, tumor necrosis factor is adsorbed onto a hydrophobic substance from the lysed culture or supernatant culture hydrophobic substance preferably is a nongelatinous hydrophobic surface such as a silicate or polyolefin, although alkyl Sepharose also is suitable. The prefered embodiment is controlled pore glass. A ratio of about 1 volume of controlled pore glass is mixed with 50 volumes of supernatant and the adsorption allowed to proceed at about 4° C. without agitation over a period of about 30 minutes to 2 hours, preferably about 1 hour, under slightly alkaline conditions. The adsorbent generally should thereafter be washed with a suitable buffer to remove entrapped contaminant proteins.

The adsorbed tumor necrosis factor is eluted from the hydrophobic substance by altering the solvation properties of the surrounding medium. The elution can be accomplished by passing a solution buffered at approximately pH 7 to 8.5, preferably around 8, containing 1M salt and an effective amount of an aqueous solution of a water miscible organic polyol, such as, for example, ethylene glycol or glycerin, ordinarily ethylene glycol in the range of 10–30 percent v/v, preferably around 20 percent v/v. Of course the optimum conditions will depend upon the polyol which is used. The tumor necrosis factor-containing elution fractions are detected by in vitro assay as described below or by other suitable assay. The purification and yield of this step from monocytic cell culture, as well as subsequent steps, are shown below in Table I.

Further purification is obtained by adsorption of tumor necrosis factor onto a tertiary or quaternary amino anion exchange resin. The preferred resins for this purpose are hydrophilic matrix resins such as cross-linked polystyrene, dextran or cellulose substituted with alkyl tertiary or quaternary amino groups. Commercial products of this type are available as DEAE cellulose, QAE Sephadex or under the trade name Mono Q (in each instance where ethyl is the alkyl substituent in each of these products). Best results are achieved with the fast protein liquid chromatography system described by J. Richey, October 1982, "American Laboratory" using the macroporous substantially uniform particles of Ugelstad et al., 1983, "Nature" 303: 95–96. This system has enabled the purification of tumor necrosis factor to a high level.

Purification to substantial homogeneity is achieved only upon further separation on SDS PAG electrophoresis or C4-reverse phase high pressure liquid chromatography (HPLC) as described in the Examples below. This product, however, is not desirable for therapy because it has lost substantial activity upon exposure to SDS or HPLC organic solvent. Protein concentration was determined by the method of M. Bradford, 1976, "Anal. Biochem." 72:248–254. During the final stages of purification, the protein concentration was estimated by amino acid composition and also by amino acid sequence.

Tumor necrosis factor is prepared for administration by mixing tumor necrosis factor having the desired degree of purity with physiologically acceptable carriers, i.e., carriers which are nontoxic to recipients at the dosages and concentrations employed. Ordinarily, this will entail combining the tumor necrosis factor with buffers, antioxidants such as ascorbic acid, low molecular weight (less than about 10 residues) polypeptides, proteins, amino acids, carbohydrates including glucose or dextrins, chelating agents

TABLE I

Purification of Human Tumor Necrosis Factor from HL-60 Cell Culture Medium

| Purification Step | Final Volumes (ml) | Total Protein (mg) | Cytolytic Activity (units) | Relative Specific Activity (units/mg) | Purification | Recovery (Percent) |
|---|---|---|---|---|---|---|
| Starting Material | 58,000 | 1,964 | $14.2 \times 10^6$ | $0.007 \times 10^6$ | — | — |
| Controlled Pore Glass Chromatography | 1,080 | 88.9 | $11.1 \times 10^6$ | $0.12 \times 10^6$ | 17 | 78.5 |
| DEAE-Cellulose Chromatography | 285 | 9.05 | $8.9 \times 10^6$ | $0.98 \times 10^6$ | 140 | 62.7 |
| Mono Q - Fast Protein Liquid Chromatography | 75 | 0.44 | $6.9 \times 10^6$ | $15.68 \times 10^6$ | 2,240 | 48.6 |
| Preparative SDS PAG Electrophoresis or | 6 | 0.028 | $2.71 \times 10^{6*}$ | $96.79 \times 10^{6*}$ | 13,387* | 19.1* |

TABLE I-continued

Purification of Human Tumor Necrosis
Factor from HL-60 Cell Culture Medium

| Purification Step | Final Volumes (ml) | Total Protein (mg) | Cytolytic Activity (units) | Relative Specific Activity (units/mg) | Purification | Recovery (Percent) |
|---|---|---|---|---|---|---|
| C4-Reverse phase-HPLC | | | | | | |

*Corrected for partial destruction of tumor necrosis factor activity caused by SDS, or by TFA and propanol.

such as EDTA, and other stabilizers and excipients. The carrier should be formulated to stabilize the tumor necrosis factor as a dimer and/or, preferably, a trimer. This is accomplished by avoiding salts or detergents in concentrations that dissociate tumor necrosis factor into monomers. Alternatively, conditions that aggregate tumor necrosis factor into higher multimers should be avoided. Generally a nonionic surfactant such as Tween 20 is employed to inhibit excessive aggregation during purification as well as lyophilization or aqueous storage. Tumor necrosis factor to be used for therapeutic administration must be sterile. This is readily accomplished by filtration through sterile filtration membranes. Tumor necrosis factor ordinarily will be stored in lyophilized form.

Tumor necrosis factor optionally is combined with other antineoplastic agents such as chemotherapeutic antibiotics (actinomycin-D, adriamycin, aclacinomycin A), or with agents to augment or stimulate the immune response, for example immunoglobulins such as gamma globulin, including immunoglobulins having affinity for the cell surface antigens of neoplasms. In addition, since interferons act synergistically with tumor necrosis factor in cell lysis assays, alpha, beta or gamma interferon is desirably combined with tumor necrosis factor compositions or tumor necrosis factor and lymphotoxin-containing compositions. A typical formulation comprises tumor necrosis factor and gamma interferon in a unit activity proportion of about from 0.1:1 to 200:1, ordinarily 10 to 1, and may contain lymphotoxin in place of a proportion of tumor necrosis factor. These proportions, of course, are subject to modification as required by therapeutic experience.

Tumor necrosis factor compositions are administered to tumor-bearing animals. The route of administration is in accord with known methods, e.g. the intravenous, intraperitoneal, intramuscular, intralesional infusion or injection of sterile tumor necrosis factor solutions, or by timed release systems as noted below. Tumor necrosis factor is administered intralesionally, i.e., by direct injection into solid tumors. In the case of disseminated tumors such as leukemia, administration is preferably intravenous or into the lymphatic system. Tumors of the abdominal organs such as ovarian cancer are advantageously treated by intraperitoneal infusion using peritoneal dialysis hardware and peritoneal-compatible solutions. Ordinarily, however, tumor necrosis factor is administered continuously by infusion although bolus injection is acceptable.

Tumor necrosis factor desirably is administered from an implantable timed-release article. Examples of suitable system for proteins having the molecular weight of tumor necrosis factor dimers or trimers include copolymers of L-glutamic acid and gamma ethyl-L-glutamate (U. Sidman et al., 1983, "Biopolymers" 22 (1): 547–556), poly(2-hydroxyethyl-methacrylate) (R. Langer et al., 1981, "J. Biomed. Mater. Res." 15: 167–277 and R. Langer, 1982, "Chem. Tech." 12: 98–105) or ethylene vinyl acetate (R Langer et al., Id.). This article is implanted at surgical sites from which tumors have been excised. Alternatively, tumor necrosis factor is encapsulated in semipermeable microcapsules or liposomes for injection into the tumor. This mode of administration is particularly useful for surgically inexcisable tumors, e.g. brain tumors.

The amount of tumor necrosis factor that is administered will depend, for example, upon the route of administration, the tumor in question and the condition of the patient. Intralesional injections will require less tumor necrosis factor on a body weight basis than will intravenous infusion, while some tumor types, e.g., solid tumors appear to be more resistant to tumor necrosis factor than others, e.g. leukemic. Accordingly, it will be necessary for the therapist to titer the dosage and modify the route of administration as required to obtain optimal cytotoxic activity towards the target tumor, as can be determined for example by biopsy of the tumor or diagnostic assays for putative cancer markers such as carcinoembryonic antigen, in view of any recombinant toxicity encountered at elevated dosage. Ordinarily, tumor necrosis factor dosages in mice up to about 120 micrograms/kg body weight/day by intravenous administration have been found to be substantially nontoxic and efficacious in vivo.

Tumor necrosis factor is not believed to be species specific in its cytotoxic activity, so that tumor necrosis factor other than human tumor necrosis factor, e.g. from bovine or porcine sources, might be employed in the therapy of human tumors. However, it is desired to use tumor necrosis factor from the species being treated in order to avoid the potential generation of autoantibodies.

In order to simplify the Examples certain frequently occurring methods will be referenced by shorthand phrases.

Plasmids are designated by a low case p preceded and/or followed by capital letters and/or numbers. The starting plasmids herein are commercially available, are publically available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133–134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103–6114, and D. Goeddel et al., 1980, "Nucleic Acids Res." 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503–517, and hybridization as described by T. Maniatis et al., 1978, "Cell" 15: 687–701.

"Transformation" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All literature citations are expressly incorporated by reference.

EXAMPLE 1

Assays

The specific activity of tumor necrosis factor was determined by a previously described modified cell lytic assay (B. Spofford, 1974, "J. Immun." 112: 2111). Mouse L-929 fibroblast cells (ATCC CCL-929) were grown in 96 well flat bottomed trays (3040; Falcon Plastics, Oxnard, Calif.) at 30,000 cells (vol 0.1 ml) per well in the presence of 1 μg/ml of actinomycin D and a serially diluted test sample (0.125 ml). The cells were incubated in a humidified atmosphere at 37° C. with 5 percent $CO_2$. The test sample was removed after 18 h, the plates were washed and cell lysis was detected by staining the plates with 0.5 percent solution of crystal violet in methanol:water (1:4)(v/v). The endpoint on the microtiter plates was determined by a Microelisa autoreader (Dynatech) set for absorption at 450 nm and transmission at 570 nm. The cells exposed to culture medium alone were set at 0 percent lysis and those exposed to 3M guanidine hydrochloride solution provided an end point for 100 percent lysis. One unit of tumor necrosis factor is defined as the amount of tumor necrosis factor (when assayed in the 0.125 ml volume) which is required for 50 percent cell lysis.

Tumor necrosis factor also was tested in an in vivo tumor necrosis assay. Briefly, this assay was carried out by growing Meth A Sarcoma cells ($5 \times 10^5$ cells) in $CB6F_1$ female mice $(BALB/c \times C57BL/6)F_1$ for 7–10 days and then injecting intratumorly with a sample of tumor necrosis factor. After 24 hrs, mice were sacrificed by cervical dislocation, tumors were removed and the necrosis was scored histologically as previously described in E. Carswell et al., 1975, "Proc. Nat. Acad. Sci." 72:3666–3670.

EXAMPLE 2

Use of PBLs or a Monocytic Cell Line to Synthesize Tumor Necrosis Factor

An HL-60 human promyelocytic cell line seed culture having a cell density of $1 \times 10^5$ cells/ml was grown in 2-liter roller bottles (890 $cm^2$) using 500 ml of RPMI 1640 medium (Irvine Scientific, Santa Ana, Calif.) containing 10 mM HEPES, 0.05 mM β-mercaptoethanol, 100 units/ml penicillin, 100 μg/ml streptomycin and 10 percent fetal calf serum. After three days at 37° C., when the culture reached a cell density of $8-12 \times 10^5$ cells/ml, cells were harvested by centrifugation at 1000 g for 10 min., washed twice with serum free RPMI 1640 medium and transferred into the same medium as described above without serum at a cell density of $15-20 \times 10^5$ cells/ml. Cells were grown in 2-liter roller bottles in the presence of 10 ng/ml PMA. After 16–24 h, the cells were removed by filtration through a 3 μm Sealkleen filter (Pall Trinity Micro Corp. Cortland, N.Y.). The clear filtrate was assayed for tumor necrosis factor activity and used for subsequent purification and characterization. This procedure produced about 400 units of tumor necrosis factor units/ml of supernatant culture medium.

Human peripheral blood monocytes were also used for the production of tumor necrosis factor. Plateletpheresis residues were obtained from American Red Cross, Boston, Mass., and used within 24 h of collection. The initial separation of monocytes from erythrocytes was achieved by centrifugation on Ficoll-Hypaque gradients at 1000 g for 30 minutes. Cells collected at the interface were washed three times with phosphate buffered saline. Monocytes derived from each donor were grown separately in 2-liter roller bottles in serum free RPMI 1640 medium at a cell density of $2.5 \times 10^6$ cells/ml. 1 μg/ml each of Staphlococcal enterotoxin B (SEB) and recombinant thymosin α-1 were added to the culture and the cells incubated in a humidified atmosphere at 37° C. with 10 percent $CO_2$. After 24–72 h, depending upon the donor, the cell supernatants were harvested and processed in a similar manner to those derived from the HL-60 cell line. Tumor necrosis factor yields from PBL cultures varied widely, depending upon the inducing agents employed. Adding PMA to the induction system described above increased the cytolytic activity of cell supernatants. However, the cell supernatants contained both tumor necrosis factor and lymphotoxin (determination of lymphotoxin or tumor necrosis factor in mixtures of tumor necrosis factor and lymphotoxin was made by conducting the cell lytic assay with test samples preincubated with rabbit neutralizing antibody to tumor necrosis factor or lymphotoxin and determining residual activity in the L-929 cell lytic assay).

EXAMPLE 3

Controlled Pore Glass Bead Chromatography

Tumor necrosis factor activity from cell culture was batch absorbed to controlled pore glass beads (Catalogue No. CPG 00350, Electro-Nucleonics, Fairfield, N.J.) equilibrated with 10 mM sodium phosphate buffer, pH 8.0, by constant stirring at 4° C. One hundred ml of glass beads were used per 5 liters of medium. After stirring for one hour, beads were allowed to settle and the supernatant was decanted off. The beads were then poured into a 5×50 cm column at room temperature and washed with 10 mM sodium phosphate buffer, pH 8.0, containing 1M NaCl. The tumor necrosis factor activity was eluted from glass beads with 20 percent ethylene glycol in 10 mM sodium phosphate buffer, pH 8.0, containing 1M NaCl. The elution profile of the HL-60 supernatant from the column is shown in FIG. 1.

EXAMPLE 4

DEAE Cellulose Chromatography

Figure 2:
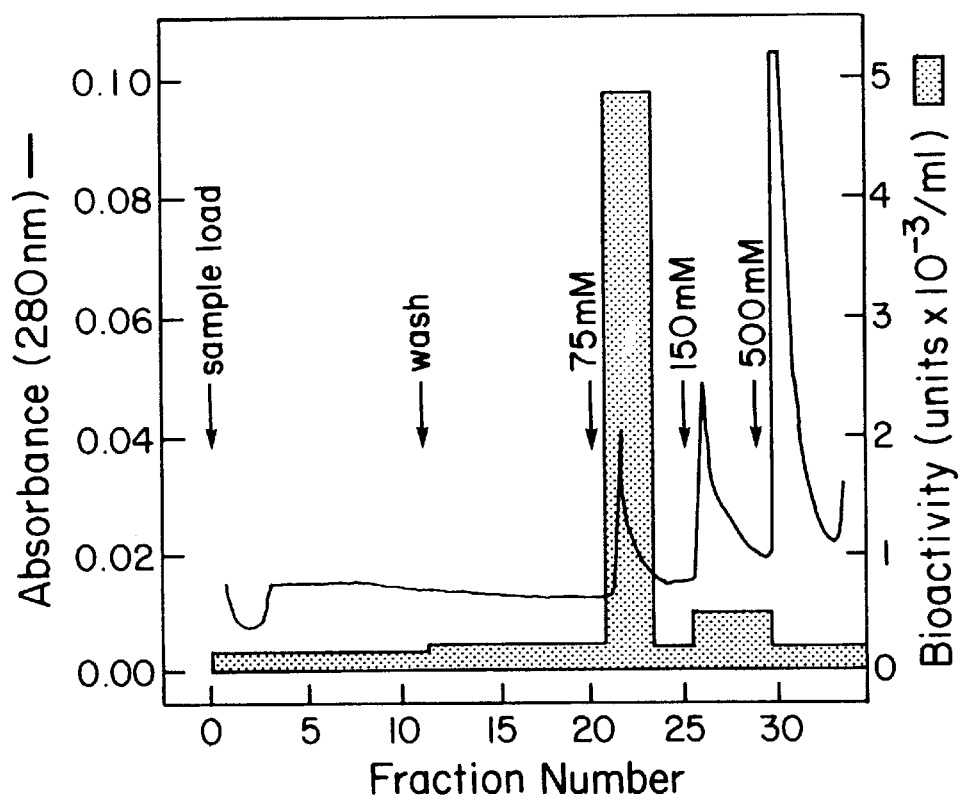
FIG. 2 shows the elution profile of tumor necrosis factor from diethylaminoethyl cellulose.

The eluate from Example 3 was directly applied to a DEAE cellulose 53 (Whatman) column (2.5×20 cm) equilibrated with 10 mM sodium phosphate buffer at pH 8.0 and 0.01 percent Tween 20, at a flow rate of approximately 500 ml/h. After the flow rate of the column was adjusted to 100 ml/h, $4.2 \times 10^6$ units of tumor necrosis factor in 1,080 ml of sample was loaded at 4° C., the column was washed with equilibration buffer and eluted with step-up gradients of 75 mM 150 mM and 500 mM sodium chloride in 10 mM phosphate buffer (pH 8.0). The eluate was monitored for absorbance at 280 nm and tumor necrosis factor activity as a function of elution fractions. The results are shown in FIG. 2.

EXAMPLE 5

Fast Protein Liquid Chromatography

Figure 3:
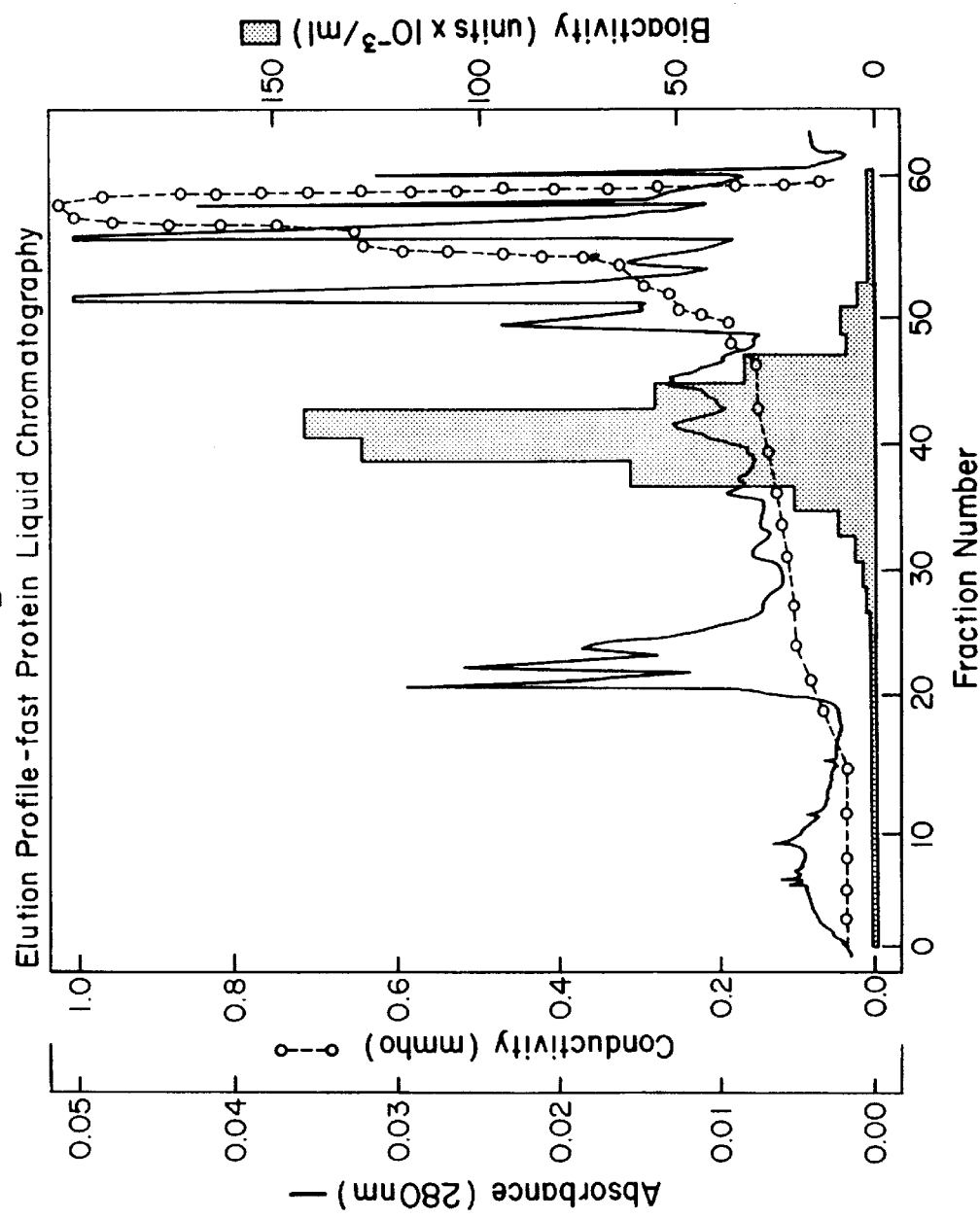
FIG. 3 shows the elution profile of tumor necrosis factor from Fast protein liquid chromatography.

The tumor necrosis factor active fraction from Example 4 was concentrated and dialyzed against 20 mM Tris HCl, pH 8.0, containing 0.01 percent Tween 20 and 1 mM sodium azide (buffer A) in an Amicon stir cell using a YM-10 membrane or other dialysis membrane with a molecular weight cut-off below that of TNF. The membrane was washed twice with buffer A. A quaternary ammonium-group substituted Sepharose bead column (9.8 μM beads in a 5×0.5 cm column; sold as Mono Q resin, Pharmacia) in a fast protein liquid chromatography (FPLC) unit (Pharmacia) equipped with a gradient programmer (GP-250) and two pumps (P-500), was preequilibrated with dialysis buffers via a superloop at a flow rate of 1 ml/min as further described in J. Richey, "American Laboratory" October 1982, page 1. The pooled washes and dialysis concentrate were loaded on the column, the column was washed with buffer A and then eluted with a linear gradient of 40–75 mM sodium chloride in buffer A. Linear gradients were programmed as follows: 0–5 min equilibration buffer; 5.1–15 min, 25 mM NaCl; 15.1–25 min, 40 mM NaCl; 25–60 min, 40–75 mM NaCl linear gradient; 60–65 min, 75 mM NaCl; 65.1–70 min, 100 mM NaCl; 70–80 min, 100–1000 mM NaCl linear gradients; 80–90 min, 100 mM NaCl; 90.1–110 min, equilibration buffer. The effluent was taken as 2 ml per fractions and monitored for absorbance at 280 nm, conductivity, and for tumor necrosis factor activity. The results are shown in FIG. 3.

EXAMPLE 6

Chromatofocusing

Figure 4:
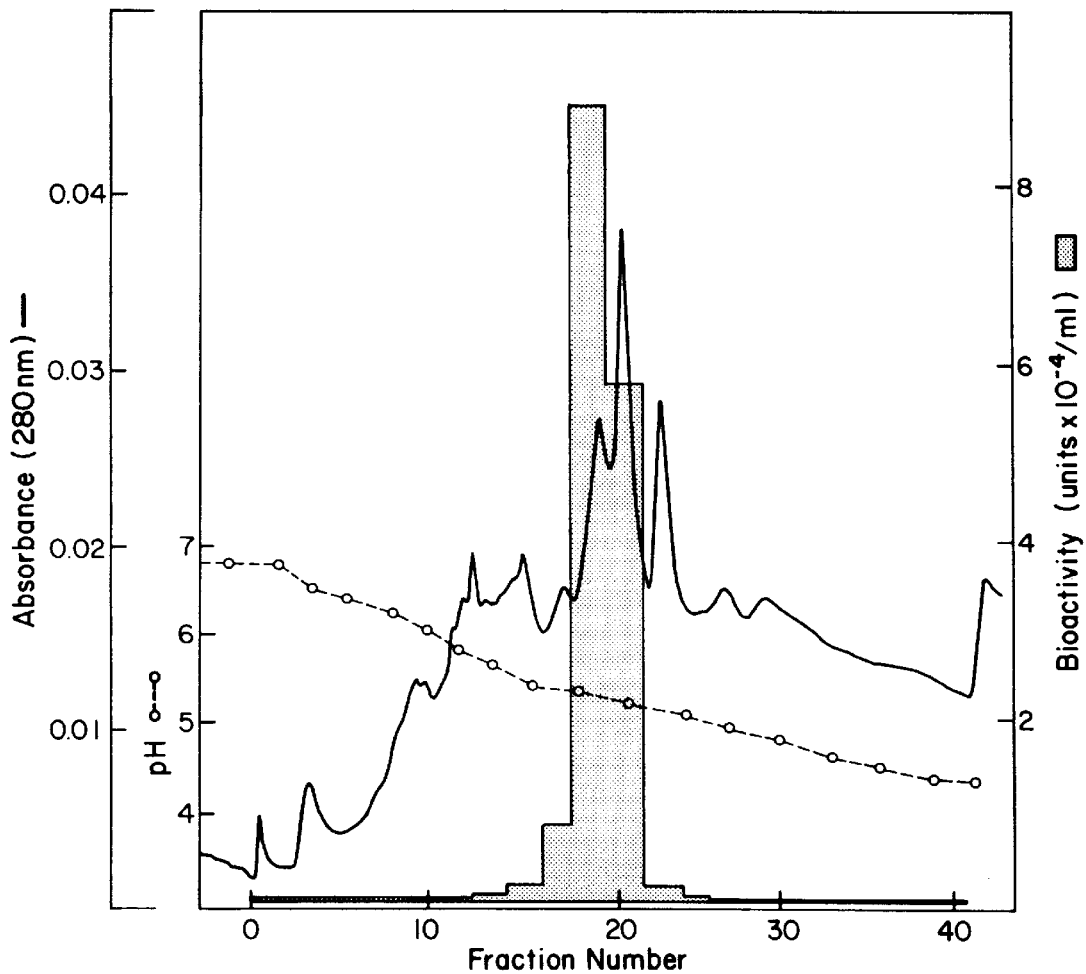
FIG. 4 shows the elution profile of tumor necrosis factor upon chromatofocusing.

Chromatofocusing was performed using a Pharmacia Mono P column (20×0.5 cm) in an FPLC system as in Example 5. The biologically active (tumor necrosis factor) fraction eluted in fraction numbers 37 to 45 from Example 5 was concentrated and dialyzed on an Amicon stir cell with a YM-10 membrane against the column equilibration buffer, i.e., 0.025 M bis-Tris HCl, pH 6.7. The sample was loaded onto the Mono P column at room temperature via a superloop at a flow rate of 1 ml/min. The column was washed with equilibration buffer until the absorbance at 280 nm returned to baseline and then eluted with a linear pH gradient established by washing the column with 7.5 percent polybuffer 74 at pH 4.7 (Pharmacia). One ml fractions were collected and the absorbance at 280 nm and pH of the effluent recorded. The results are shown in FIG. 4. As can be seen from FIG. 4, the isoelectric point of tumor necrosis factor was about 5.3.

EXAMPLE 7

Preparative SDS-Polyacrylamide Gel Electrophoresis

Fifteen percent polyacrylamide gels (11×16 cm) with a thickness of 1.5–3.0 mm were prepared according to a modification of the procedure of U. Laemmli, 1970, "Nature" 227:680–685. Both resolving and stacking gels contained 0.1 percent SDS and 0.05 percent Tween 20. Other buffers and concentration of cross linking reagent were the same as for analytical SDS-PAGE gels. Tumor necrosis factor active fractions from Examples 5 or 6 step were pooled, concentrated and dialyzed against 6.25 mM Tris HCl, pH 7.0, containing 0.005 percent SDS on an Amicon stir cell using a YM-10 membrane. After removal of the dialyzed concentrate, the membrane was washed three times with a small volume of sample buffer (0.2 percent SDS, 0.02 percent Tween 20, 30 percent glycerol, 0.03M Tris HCl, pH 6.8, 0.005 percent tracking dye). The dialyzed concentrate and washes were pooled (total volume 1–4 ml), mercaptoethanol optionally added to establish SDS PAGE reducing conditions, and the sample loaded into a large well cast in the stacking gel. Small wells adjacent to the sample well were used for prestained molecular weight markers phosphorylase-a (94K), bovine serum albumin (67K), ovalbumin (43K), carbonic anhydrase (30K), soybean trypsin inhibitor (20K) and Lysozyme (14.4K). The gels were run in a Biorad vertical electrophoresis system cooled to 12° C., at a constant current of 20 mA per mm of gel thickness, until the tracking dye reached the bottom of the gel.

Figure 5:
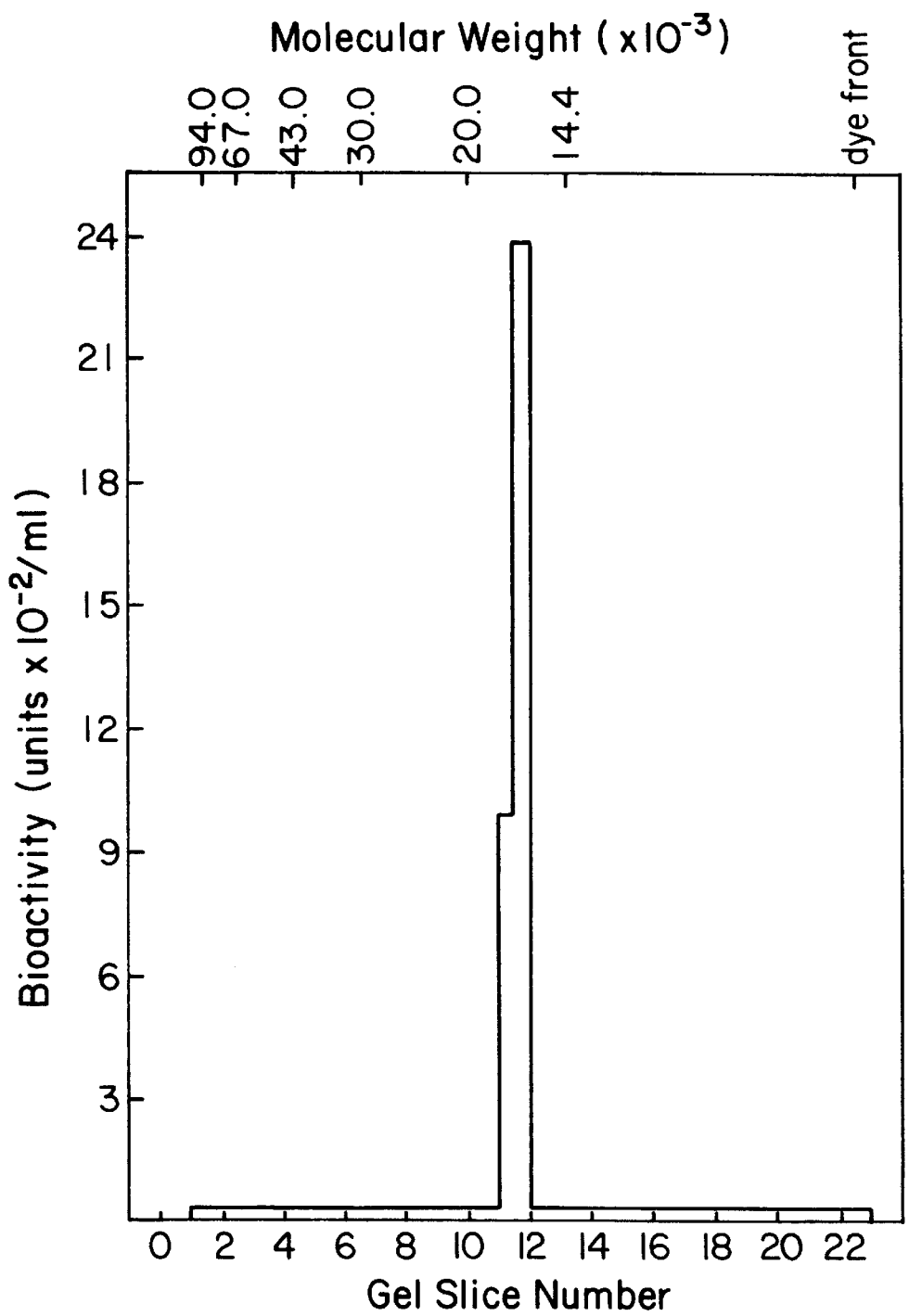
FIG. 5 shows the molecular weight of tumor necrosis factor by SDS PAGE gel electrophoresis.

Following electrophoresis, one of the glass plates was removed from the gel, and the positions of the molecular weight markers were noted. The lane containing the applied tumor necrosis factor sample was then cut into 0.25 cm sections in accord with the molecular weights of the marker proteins. These gel slices were then placed in polypropylene tubes containing 1–2 ml of 10 mM ammonium bicarbonate and 0.01 percent Tween 20, pH 8, and allowed to elute for 16 h at 4° C. The eluates were then assayed for tumor necrosis factor activity and the results shown in FIG. 5. The tumor necrosis factor molecular weight on SDS gel was about 17,000, whether under reducing or nonreducing conditions, thus indicating a single chain molecule.

The protein was recovered from the eluate of gel slices free of salts and low molecular weight substances by the following treatment: Small columns were prepared containing 0.2 ml Sep-pak C18 resin, which had been pre-washed with acetonitrile, 1-propanol, 1 percent trifluoroacetic acid (TFA), and distilled water and then equilibrated with 10 mM ammonium bicarbonate containing 0.01 percent Tween-20, pH 8.0. The gel eluate was loaded onto the column and the effluent collected. The resin was then washed with approximately 5 ml each of distilled water and 0.1 percent TFA, to remove free amino acids and buffer salts. Tumor necrosis factor was eluted from the resin with 1 ml of 50 percent 1-propanol in 0.1 percent TFA. Further elutions with 1 ml each of 50 percent 1-propanol in 1 percent TFA, and 99 percent 1-propanol in 1 percent TFA were also performed, but the protein was usually eluted with the first buffer. Approximately 80 percent of the tumor necrosis factor bioactivity was inactivated in this step. While the tumor necrosis factor so obtained can be employed for sequence analysis it is preferred that the HPLC effluent described below in Example 8 be used for this purpose.

EXAMPLE 8

Hiqh Pressure Liquid Chromatography

Figure 6:
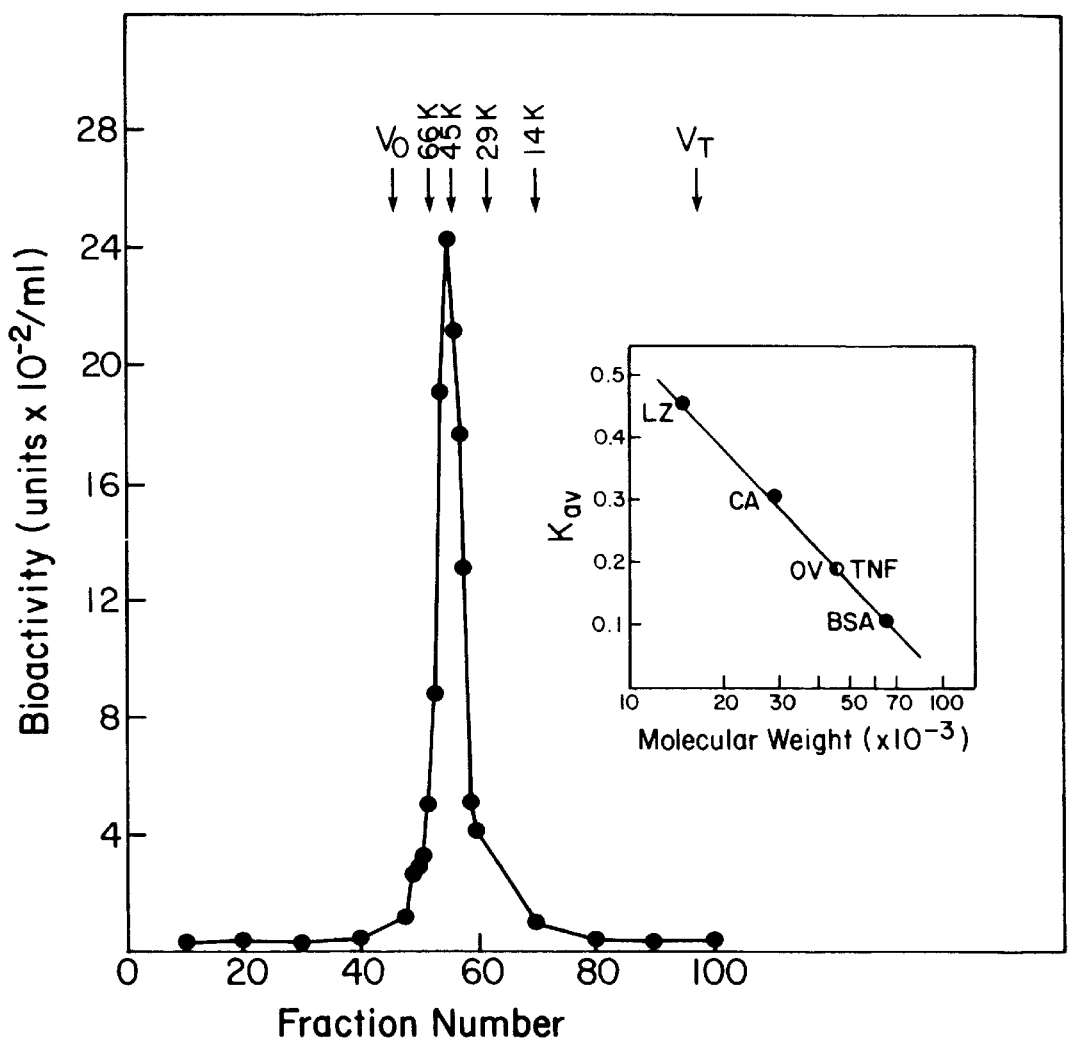
FIG. 6 shows the molecular weight of tumor necrosis factor upon HPLC elution.

The molecular weight of native intact tumor necrosis factor was determined by high pressure gel permeation chromatography. The latter was carried out at room temperature using a TSK G2000 SW gel HPLC column (Alltech Associates, Deerfield, Ill.)(7.5×60 mm). A one ml sample of purified tumor necrosis factor from Example 5 containing approximately 1 µg of protein and 15,600 units of activity was isocratically eluted from the gel column at a flow rate of 0.5 ml/min, with 0.2M sodium phosphate buffer, pH 7.0. The column was calibrated with bovine serum albumin (MW 66,000), ovalbumin (MW 45,000), bovine carbonic anhydrase B (MW 29,000), and lysozyme (MW 14,300). One ml fractions were obtained and assayed for tumor necrosis factor activity. The fractions showing tumor necrosis factor activity eluted consistent with a molecular weight of 45,000±6,000 (FIG. 6).

EXAMPLE 9

Reverse-phase HPLC

Figure 7:
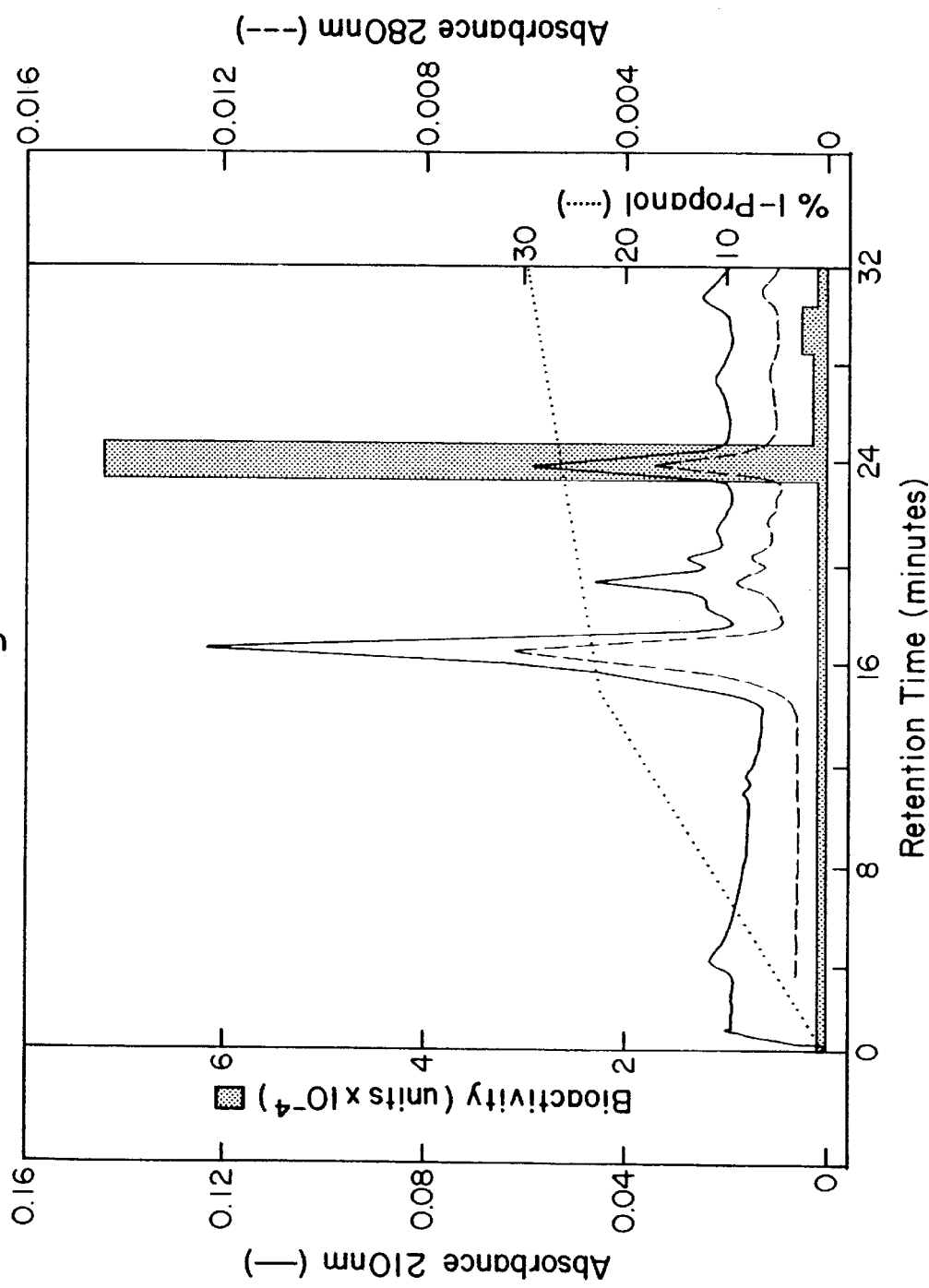
FIG. 7 shows the elution profile of tumor necrosis factor from an HPLC C4 column.

Tumor necrosis factor also was purified by reverse-phase HPLC using C4 Synchropak columns on Water's Associates, Inc. chromatograph system as described previously (W. Kohr et al, 1982, Anal. Biochem, 122: 348–359). Protein peaks were detected at 210 nm and at 280 nm after elution with a linear gradient of 1 to 23 percent v/v 1-propanol in 0.1 percent aqueous TFA in the first 15 minutes and 23–30 percent v/v 1-propanol in 0.1 percent TFA for the next 15 minutes at a flow rate of one ml per minute. The peaks were assayed for cytolytic activity. The organic solvents employed in eluting tumor necrosis factor from the C4 column reduced tumor necrosis factor activity about 80 percent. Tumor necrosis factor purified by this method was dried under vacuum, and then processed for amino acid analysis and sequencing. The results are recorded in FIG. 7. FIG. 7 shows that the tumor necrosis factor obtained in the effluent from Example 5 contained biologically inactive protein contaminants eluting at about 16 and 19 minutes retention time. The bioactive effluent from C4-RP-HPLC was substantially homogeneous, by the criteria of amino terminal sequence.

EXAMPLE 10

Determination of Partial Amino Acid Sequence for Tumor Necrosis Factor

Figure 8:
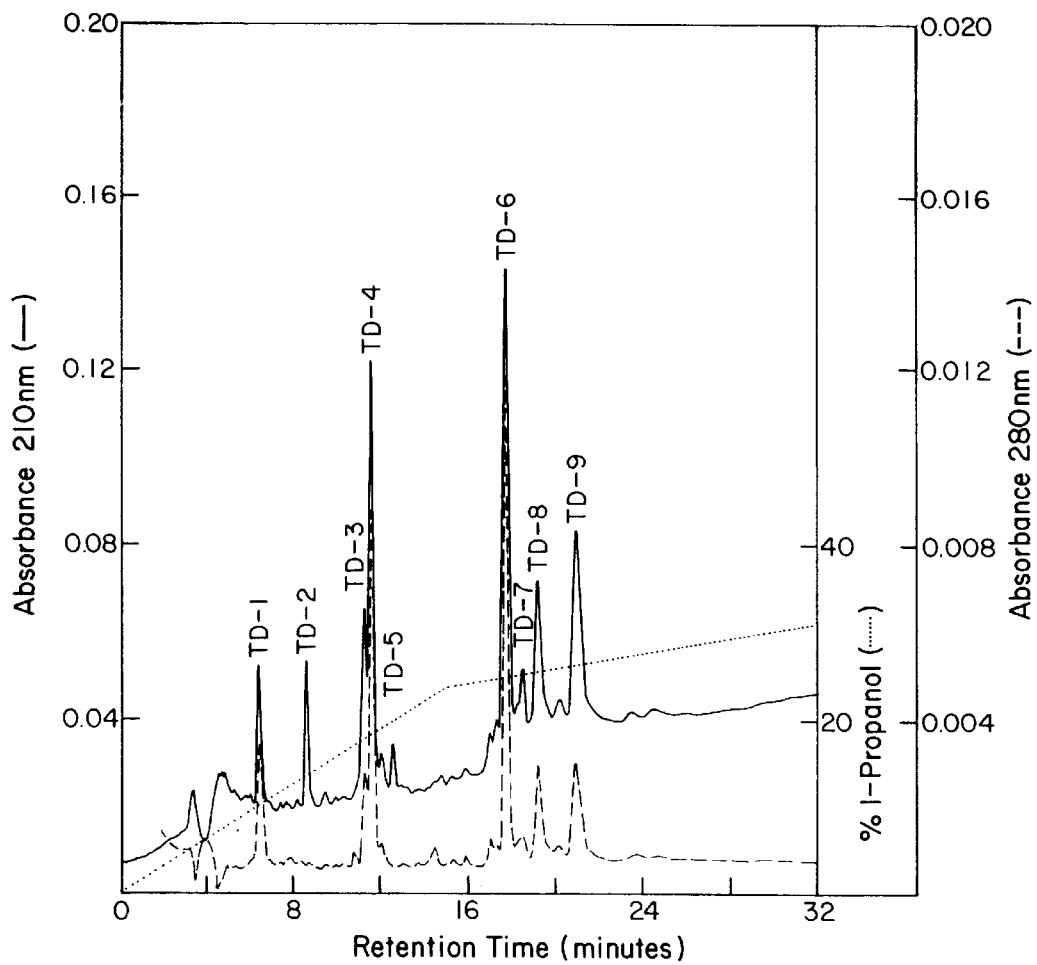
FIG. 8 illustrates the separation of tumor necrosis factor trypsin digest fragments on HPLC.

Tumor necrosis factor was trypsin digested as follows: Homogeneous tumor necrosis factor from Example 9 was dissolved, dried down and redissolved in 100 mM of ammonium bicarbonate buffer pH 8.0 containing 5 percent w/w TPCK trypsin. (Worthington Biochemicals), 1 mM $CaCl_2$ and 0.01 percent Tween-20 at an enzyme to substrate ratio of 1:20, incubated for 6 hours at 37° C., an additional 5 percent by w/w of trypsin added and the hydrolysis mixture further incubated for 12 hours at 37° C. The reaction mixture was applied onto C4 HPLC as described above in order to separate the peptide fragments. The results are shown in FIG. 8. A total of 9 fragments were observed (fragments 2 and 2' eluted together at the peak designated T2 in FIG. 8). An additional tenth fragment is believed to not be retained by the column. Amino acid sequences for intact tumor necrosis factor from Examples 8 and 9 and the trypsin hydrolysis fragments obtained in this Example were determined by automated sequential Edman degradation using a modified Beckman sequencer model 890B equipped with cold traps. Polybrene (1.25 mg) was used as a carrier in the cup. Based on the amino acid composition of the intact molecule, the molecular weight of intact tumor necrosis factor is 17,100. This figure was consistent with the SDS-PAGE data and constitutes confirmation of the absence of glycosylation.

EXAMPLE 11

Synergistic Action of Tumor Necrosis Factor and Gamma Interferon

Figure 9:
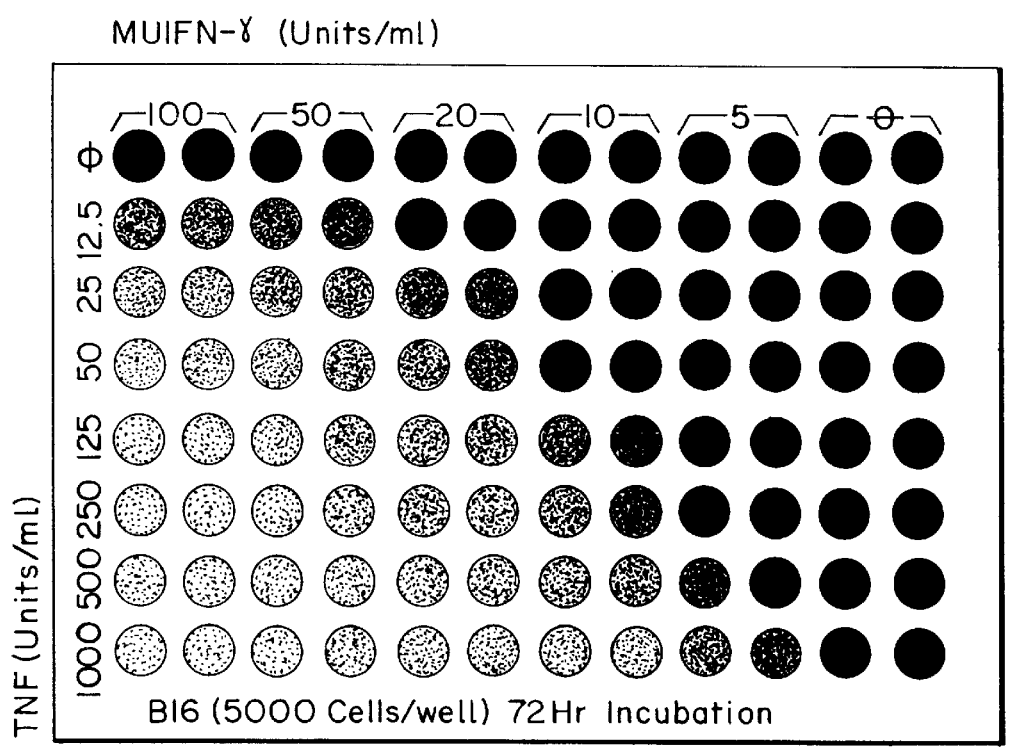
FIG. 9 illustrates the cytotoxic effect of gamma interferon and tumor necrosis factor mixtures.

Cells of the murine melanoma B16, (Mason Research, Worcester, Mass.) a cell line of C57B1/6 origin, were seeded in a microtiter plate at 5,000 cells/well and incubated for 4 hours at 37° C. in a 5 percent $CO_2$-humidified incubator before the addition of the lymphokines. Tumor necrosis factor obtained from Example 1 was purified to substantial homogeneity by HPLC and quantitated by its activity in the above-described bioassay for cytolysis of L929 cells. Similarly, purified recombinant murine gamma interferon (P. Gray et al., 1983, "Proc. Natl. Acad. Sci. U.S.A." 80: 5842–5846) was assayed by its antiviral activity against EMC-infected L cells (D. Goeddel et al., 1980, "Nature" (London) 287: 411–416). Murine gamma interferon and human tumor necrosis factor were separately diluted to the dilutions shown in FIG. 9. Gamma interferon was added first to the designated wells, and diluted tumor necrosis factor was added immediately thereafter, to a final volume of 0.2 ml/well. At the end of 72 hours of incubation, the cells were stained with 0.5 percent crystal violet in 20 percent methanol. The results are shown in FIG. 9. B16 is relatively resistant to either tumor necrosis factor or IFN-γ alone; at 1,000 units/ml of tumor necrosis factor no visually detectable cytolysis was observed. However, addition of very small amounts of gamma interferon (as little as 5 units/ml) resulted in cytolysis.

EXAMPLE 12

Messenger RNA Isolation

Total RNA from HL-60 cell cultures (4 hours after PMA induction) or peripheral blood monocytes cultured as described in Example 2 was extracted essentially as reported by Ward et al., 1972, "J. Virol." 9: 61. Cells were pelleted by centrifugation and then resuspended in 10 mM NaCl, 10 mM Tris-HCl pH 7.5, 1.5 mM $MgCl_2$. Cells were lysed by the addition of NP-40 (1 percent final concentration), and nuclei were pelleted by centrifugation. The supernatant contained the total RNA which was further purified by multiple phenol and chloroform extractions. The aqueous phase was made 0.2 M in NaCl and then total RNA was precipitated by the addition of two volumes of ethanol. A typical yield from 1 gram of cultured cells was about 6 milligrams of total RNA. Polyadenylated mRNA (about 100 µg) was obtained on oligo (dT) cellulose by the method of H. Aviv et al., 1972, "Proc. Natl. Acad. Sci. U.S.A." 69: 1400–1412.

EXAMPLE 13 cDNA Library 7.5 µg of poly(A)+ mRNA from Example 12 was converted to double stranded cDNA by the successive action of reverse transcriptase, DNA polymerase Klenow fragment, and S1 nuclease (P. Gray et al., 1982, "Nature" 295: 503–508; M. Wickers et al., 1978, "J. Biol. Chem." 253: 2483–2495). About 80 ng of cDNA having greater than 600 bp in length were isolated from a polyacrylamide gel.

The synthetic DNA adaptor sequence 5'AATTCAT-GCGTTCTTACAG 3'/3'GTACGCAAGAATGTC 5' was ligated to the cDNA to create EcoRI cohesive termini. As is conventional in the art, the adaptor was synthesized chemically as two separate strands, the 5' end of one of the strands was phosphorylated with polynucleotide kinase and the two strands annealed. The cDNA (20 ng) was then re-isolated from a polyacrylamide gel, inserted by ligation into EcoRI-digested λgt-10, packaged into phage particles and propagated in E. coli strain C600 hfl (Huynh et al., 1984, Practical Approaches in Biochemistry, IRL Press Ltd., Oxford England) or other known strain suitable for lamda phage propagation. A cDNA library of about 200,000 independent clones was obtained.

EXAMPLE 14

Preparation of a Deoxyoliqonucleotide Probe for Tumor Necrosis Factor cDNA

A 42 nucleotide DNA hybridization probe, based upon the preliminary amino acid sequence of tumor necrosis factor tryptic peptide TD-6 (E-T-P-E-G-A-E-A-K-P-W-Y-E-K-) was designed on the basis of published codon usage frequencies (R. Grantham et al., 1981 "Nucleic Acids Res." 9: 43–74), and the codon bias of human IFN-γ (P. Gray et al., 1982, "Nature" 295: 503–508), and human lymphotoxin The preliminary sequence was in error (the final K should have been P). Nonetheless, this sequence led to a successful probe. The synthetic probe had the sequence 5'dGAAAC-CCCTGAAGGGGCTGAAGCCAAGCCCTGG-TATGAAAAG 3' and was synthesized by the method of R. Crea et al., 1980, "Nucleic Acids Res." 8: 2331–2348. The probe was phosphorylated with (λ-$^{32}$P) ATP and T4 polynucleotide kinase as described previously (Goeddel et al., 1979, "Nature" 281: 544).

EXAMPLE 15

Identification of a cDNA Clone Containing Tumor Necrosis Factor Coding Sequences About 200,000 recombinant phage from the λgt 10 cDNA library were screened by DNA hybridization using the $^{32}$P-labelled 42-mer from Example 14 under conditions of low stringency in accordance with A. Ullrich et al., 1984, "EMBO J." 3: 361–364 (or alternatively P. Gray et al., 1983, "Proc. Natl. Acad. Sci. U.S.A." 80: 5842–5846, S. Anderson et al., 1983, "Proc. Natl. Acad. Sci. U.S.A." 80: 6836–6842 and M. Jaye et al., 1983, "Nucleic Acids Res." 11: 2325–2335). Nine distinct clones hybridized with the probe and were plaque purified. Then $^{32}$P-labelled cDNA was prepared using mRNA from uninduced HL-60 cells. DNA from seven of these nine phage clones failed to hybridize with this "uninduced" probe and were therefore judged to be candidates for tumor necrosis factor cDNA sequences. The cDNA clone containing the largest insert was designated λ42-4. This insert was sequenced by the dideoxy chain termination method (A. Smith, 1980, "Methods in Enzymology" 65: 560–580 and F. Sanger et al., 1977, "Proc. Natl. Acad. Sci. U.S.A." 74: 5463–5467) after subcloning into the vector M13mp8 (J. Messing et al., 1981, "Nucleic Acids Res." 9: 309–321).

The cDNA sequence obtained for λ42-4 contained the entire coding region for mature tumor necrosis factor plus a portion of its signal peptide. The correct orientation and reading frame of the DNA was deduced by comparison with the amino acid sequence of tryptic peptide T4 of tumor necrosis factor. The amino terminal valine residue of tumor necrosis factor determined by protein sequencing is indicated as amino acid 1, and is followed by 156 additional amino acids before a stop codon in reading phase is encountered. The calculated molecular weight is 17,356 daltons.

EXAMPLE 16

Identification of a cDNA Clone Containing Complete PreTNF Coding Sequences

The cDNA clone λ42-4 contains the entire coding region of mature TNF but lacks a complete signal peptide coding sequence as evidenced by its lack of an initiation codon. To obtain the missing sequence information, the hexadecanucleotide primer dTGGATGTTCGTCCTCC was chemically synthesized. This primer was annealled to mRNA from Example 12 and then cDNA was synthesized using the method of Example 13. A new library of about 200,000 cDNA clones was prepared in λgt10 following the method described in Example 13. This library was screened by hybridization analysis using as a probe the λ42-4 cDNA insert which had been $^{32}$P-labelled. Sixteen positive clones were obtained, the longest (λ16-4) of which contained a cDNA insert extending 337 bp further 5' than the λ42-4 insert. The composite sequence of the TNF cDNA inserts of λ16-4 (nucleotides 1–870) and λ42-4 (nucleotides 337–1643) contained the complete TNF cDNA (nucleotides 1–1643).

EXAMPLE 17

Figure 11:
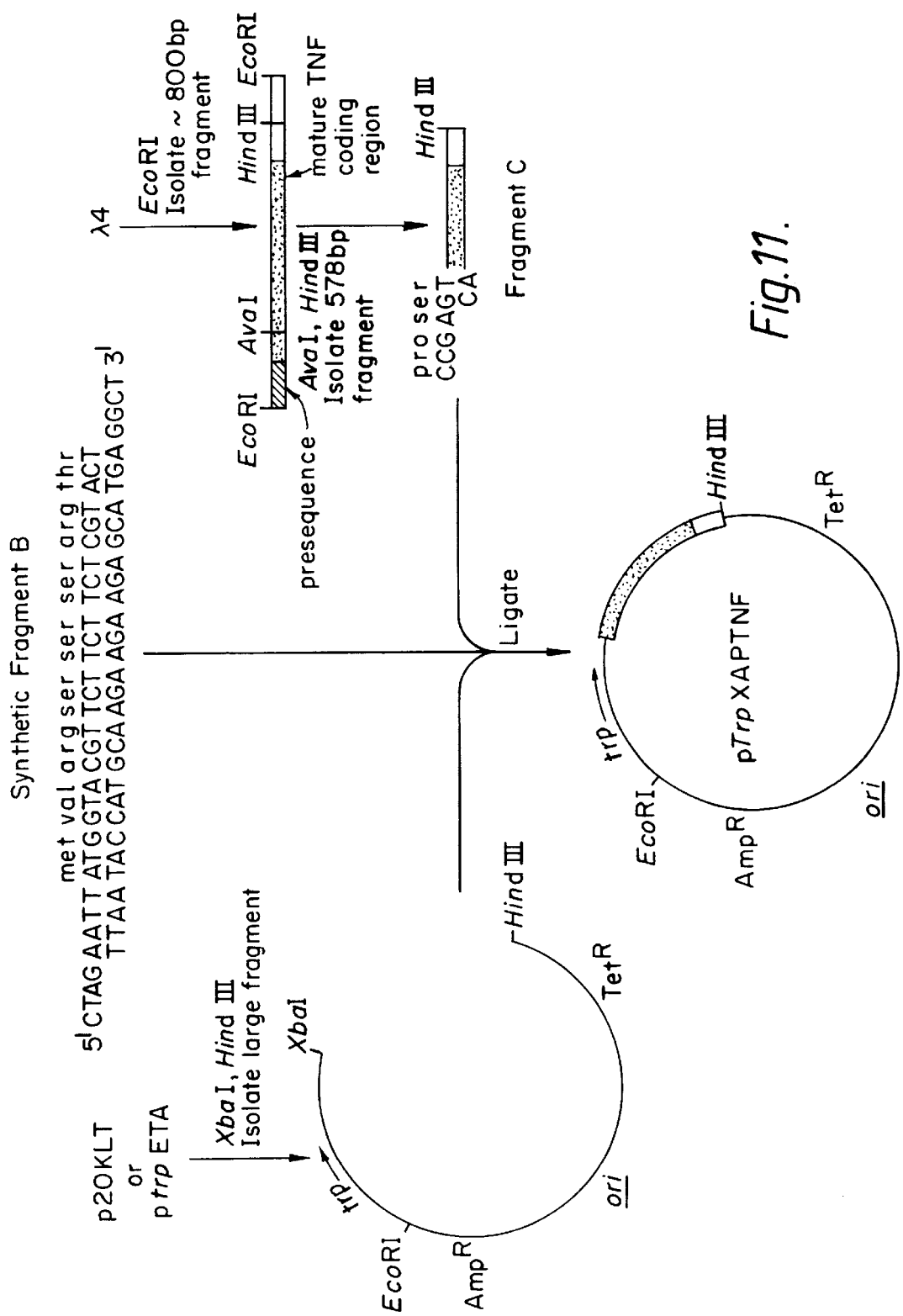
FIG. 11 shows the construction of a tumor necrosis factor expression vector.

Construction of an Expression Vector for Direct Expression of Tumor Necrosis Factor The procedure used to express the cDNA sequence for tumor necrosis factor obtained in Example 15 is set forth in FIG. 11. Phage λ42-4 from Example 15, containing the entire mature tumor necrosis factor coding sequence and a portion of the putative tumor necrosis factor secretory leader, was digested with EcoRI and an approximately 800 bp fragment containing the tumor necrosis factor coding region was recovered. This fragment was digested with Ava I and Hind III and a 578 bp fragment (designated "C" in FIG. 11) recovered. This fragment encodes tumor necrosis factor amino acids 8–157.

Two synthetic deoxyoligonucleotides (designated fragment "B" in FIG. 11) were prepared (see the construction of the adaptor sequence in Example 13) which incorporated an Xba I cohesive terminus at the 5' end, an Ava I cohesive terminus at the 3' end, a met initiation codon and codons for the first seven amino terminal amino acids of tumor necrosis factor. The codons for these amino acids were chosen on the basis of E. coli preference. The AATT sequence upstream from the start codon was selected to properly space the start codon from the trp ribosome binding sequence and, in combination with the amino acid codons, to eliminate a potential messenger RNA loop.

Segments B and C are then joined in a three-fold ligation with a pBR322 derivative containing the trp promoter sequence with the Shine-Dalgarno sequence of the trp leader peptide (European Patent Application Publn. No. 36776). The derivative is obtained or designed to contain unique Xba I and Hind III sites between the trp promoter and the Tet$^R$ gene. Either p20KLT (copending U.S. Ser. No. 616,503, incorporated by reference) or ptrpETA (Gray et al., 1984, "Proc. Natl. Acad. Sci. U.S.A." 81: 2645–2649) are suitable starting vectors of this type, although others may be constructed from pBR322, the trp promoter and any required synthetic linkers. Both pBR322 and plasmids containing the trp promoter are publicly available. The pBR322 portion of the vector chosen may have the AvaI-PvuII segment from bp 1424 to 2065 deleted (designated "XAP" in the plasmid name). Any of the foregoing plasmids are simultaneously digested with Xba I and Hind III and the large vector fragment recovered. This fragment, and fragments B and C are ligated with T4 DNA ligase and the ligation mixture used to transform E. coli 294 (ATCC 31446). Ampicillin resistant colonies were selected, plasmid DNA recovered and characterized by restriction endonuclease mapping and DNA sequencing. pTrpXAPTNF was obtained which contained inserts B and C.

EXAMPLE 18

Tumor Necrosis Factor Expression in E. coli

E. coli ATCC 31446 which had been transformed with pTNFtrp was grown in M9 medium containing 20 μg/ml ampicillin and the culture grown to an $A_{550}$=0.3. Indole acetic acid was added to give a final concentration of 20 μg/ml and the culture grown to $A_{550}$=1. 10 ml of cells were concentrated and resuspended in phosphate buffered saline. The cells were sonicated and diluted for tumor necrosis factor determination in the Example 1 assay. Approximately $10^5$ units of activity were obtained per ml of culture. This activity was neutralized by preincubation with rabbit antisera from rabbits immunized against human tumor necrosis factor.

EXAMPLE 19

Tumor Necrosis Factor Expression in E. coli

This method is preferred over that of Example 18.

Preferably, the host for use with the above vectors is a non-revertable tonA E. coli strain. Such strains are bacteriophage resistant and therefore far more suitable for large scale culture than wild-type strains. Following is a description of a suitable method for generating such a strain. The method is further described in copending U.S. Ser. No. 673,955. E. coli W3110 is transduced with λ::Tn10, a lambda bacteriophage containing the transposable element Tn10, to generate a Tn10 hop pool of E. coli W3110. (N. Klecker et al., 1977 "J. Mol. Biol." 116: 125).

The E. coli W3110::Tn10 hop pool is grown in L broth at 37° C. to a cell density of about 1×10$^9$/ml. 0.5 ml of the culture is centrifuged and the pellet is resuspended in 0.2 mls of a λphi80 (or T1) lysate containing 7.0×10$^9$ pfu. The phage is allowed to adsorb for 30 minutes at 37° C. The suspension is then spread on EMB plates supplemented with tetracycline (15 μg/ml). After an overnight incubation at 37° C., the light pink colonies are pooled in 3 ml of L broth, grown overnight at 37 ° C., washed twice, and resuspended in L broth. This culture is infected with bacteriophage Pl kc, and the phage lysate recovered (J. Miller, 1972, Experiments in Molecular Biology, Cold Spring Harbor Laboratory, p 304).

E. coli AT982 (no. 4546, E. coli Genetic Stock Center, New Haven, Conn.) is transduced to tetracycline resistance by this Pl kc lysate. Transductants are selected on L broth plates supplemented with tetracycline (15 μg/ml) and (40 μg/ml) dap (diaminopimelic acid). The resulting transductants are screened for tetracycline resistance and the regeneration of the dap gene (dap$^+$, tet$^R$). dap$^+$, tet$^R$ transductants are then tested for λphi80 (or T1) resistance.

P1 kc lysates are then made on several dap$^+$, tet$^R$, λphi80 (or T1) resistant strains. The lysates are used to transduce E. coli W3110 to tetracycline resistance. The transductants are screened and selected for λphi80 (or T1) resistance.

Tetracycline sensitive isolates are selected from the W3110 fhuA::Tn10-λphi80R transductants (S. Naloy et al., 1981 "J. Bact." 145: 1110). These isolates are checked for phage λphi80 resistance and tetracycline sensitivity after single colony purification.

DNA is isolated from several tetracycline sensitive λphi80 phage resistant mutants and digested with SstII. The SstII digested DNA is characterized by the Southern blot procedure using radioactively labelled and SstII digested λ::Tn10 DNA as a probe to determine if the Tn10 has excised (R. Davis et al., 1980, Advanced Bacterial Genetics, Cold Spring Harbor Laboratory). One of the tetracycline sensitive isolates is shown to have lost two of the Tn10 hybridization bands as compared to the hybridization between DNA from the λ::Tn10 and the parental W3110 fhuA::Tn10λphi80R. A third hybridization band has an altered mobility indicating that a deletion caused by the imprecise excision of Tn10 has occurred.

SDS-gel electrophoresis of outer membrane preparations from the strain with an imprecise Tn10 excision reveal that the band assumed to be the fhuA protein has an altered electrophoretic mobility as compared to the wild-type fhuA protein. The resulting protein is non-functional as a λphi80 phage receptor protein. A second independent strain which also has undergone imprecise excision of Tn10 shows no fhuA protein on the SDA gel.

Neither of these strains demonstrate reversion to tetracycline resistance or to λphi80 susceptability indicating that there is an imprecise excision of all or part of the Tn10 transposon together with either a partial or complete deletion of the fhuA gene. Preferably, one of such W3110 strains (NL106) is used as a host for the TNF-encoding vehicles described elsewhere herein.

NL106 was transformed with ptrpXAPTNF and inoculated into 10 liters of a pH 7.4 medium having the following formula:

| Component | gms/L |
| --- | --- |
| (NH$_4$)$_2$SO$_4$ | 5.0 |
| K$_2$HPO$_4$ | 6.0 |
| NaH$_2$PO$_4$ | 3.0 |
| Na Citrate | 1.0 |
| L-Tryptophan | 0.2 |

| Component | gms/L |
|---|---|
| NZ Amine AS | 4.0 |
| Yeast Extract | 4.0 |
| MgSO$_4$ | 1.2 |
| Glucose | 25.0 |
| Trace Element solution (Fe, Zn, Co, Mo, Cu, B and Mn ions) | 0.5 ml |
| Tetracycline | 1.0 mg |

Glucose was fed to the culture at a rate of 1 gm/minute when the $A_{550}$ of the culture reached about 20. The fermentation was conducted at 37° C. until an $A_{550}$ of 136 was reached (about 20 hours). The culture is centrifuged to form a cell paste and the paste then extracted for 30 min. at pH 8.0 and room temperature with a buffer containing 50 mM tris, 10 mM EDTA, 1000 mM NaCl, 2000 mM urea and 0.1 percent beta-mercaptoethanol. The extract was diluted and assayed as described in Example 1. $1\times10^8$ units of tumor necrosis factor activity in this assay was established as equivalent to 1 mg of tumor necrosis factor. Up to about 2 grams of tumor necrosis factor were obtained per liter of culture. Amino terminal sequencing demonstrated that about from 75 to 86 percent by weight was valyl amino-terminal (mature) tumor necrosis factor, the remainder being met-TNF. Furthermore, in addition to high expression levels the protein was not present in refractile bodies, nor did it otherwise appear to be toxic to the cells as evidenced by the extremely high cell densities that were obtained.

EXAMPLE 20

Construction and Expression of a Mutant Tumor Necrosis Factor Gene

In this contemplated example, Examples 17–18 were repeated except that the oligonucleotide fragment B was synthesized with a histidine codon CAT in place of the arginine 6 codon CGT. Mutant tumor necrosis was expressed.

EXAMPLE 21

Construction and Expression of Another Mutant Tumor Necrosis Factor Gene

In this example, the procedure of Examples 17–18 was repeated with an oligonucleotide fragment B encoding leucine (CTT) in place of the residue 2 arginine codon. About 1200 mg of mature TNF activity were obtained per liter of culture in initial trials. Unprocessed TNF was not detectable in the culture.

EXAMPLE 22

Construction of a Vector Encoding a Tumor Necrosis Factor Fusion with a Secretory Signal Sequence The sequence of the E. coli heat stable enterotoxin gene STII is depicted in FIG. 12. In this Example a fragment containing the STII secretory signal and Shine-Dalgarno sequence was ligated downstream of the E. coli alkaline phosphotase promoter. The STII signal is followed in the 3' direction with a synthetic oligonucleotide which supplies codons for the initial seven amino-terminal tumor necrosis factor amino acids and the remainder of the coding sequence for tumor necrosis factor. All of the foregoing were assembled in a pBR322 vector.

pWM501 (Picken et al., 1983, "Infection and Immunity" 42(1): 269–275) contains the STII gene depicted in FIG. 12. pWM501 was digested with XbaI and NsiI and the approximately 90 bp fragment isolated. This fragment also could be synthesized organically by methods known per se (fragment A).

A pBR322-Trp plasmid as described in Example 17 (p20kLT) was digested with XbaI and HindIII, and the large vector fragment recovered (fragment B). This fragment contains an E. coli origin of replication and a gene conferring the phenotype of ampicillin resistance.

A synthetic oligonucleotide was synthesized as two strands and annealed to yield the following structure (the restriction site sticky ends and amino acids coded for by the oligonucleotide are also indicated).

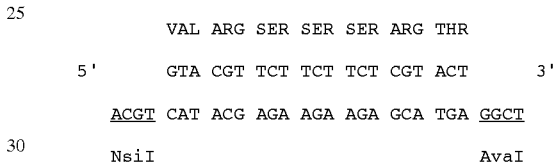

This is designated fragment C.

pTNFtrp from Example 18 was digested with AvaI and HindIII. The 578 bp AvaI-HindIII fragment (fragment D) was recovered. It contains all of the TNF coding sequence except for the first seven amino acids.

A DNA sequence comprising an E. coli alkaline phosphatase (AP) promoter linked to a heterologous Shine-Dalgarno (S.D.) sequence (trp) and having EcoRI and XbaI termini was constructed as follows. A DNA fragment containing a portion of the AP promoter was isolated from the plasmid pHI-1 (H. Inouye et al., 1981, "J. Bacteriol." 146: 668–675), although any appropriate sources containing AP promoter DNA also could be used. pHI-1 was digested with HpaI to open the plasmid, a synthetic EcoRI linker GAATTCGAATTC/CTTAAGCTTAAG ligated to the plasmid and the linkered plasmid digested with an excess of EcoRI to cleave all EcoRI site and with a deficiency of RsaI activity in order to only partially cleave all of the RsaI sites (the EcoRI and RsaI steps also could be done sequentially rather than simultaneously). A 420 bp fragment containing the AP promoter was recovered from the EcoRI-RsaI partial digest.

A trp S.D. sequence was obtained as follows. A plasmid or organism containing the trp promoter (pIFN-beta 2, D. Leung et al., 1984, "Biotechnology" 2: 458–464) was digested with XbaI and RsaI and the 30 bp fragment recovered which contains the trp S.D. sequence. This fragment was ligated to the 420 bp AP promoter fragment to yield a 450 bp EcoRI-XbaI fragment E. Fragment E has the nucleotide sequence

```
EcoRI
GAATTCAACTTCTCCATACTTTGGATAAGGAAATACAGACATGAAAAATCTCATTGCTGAGTTGTTATTT

AAGCTTGCCCAAAAAGAAGAAGAGTCGAAAGAACTGTGTGCGCAGGTAGAAGCTTTGGAGATTATCGTCA

CTGCAATGCTTCGCAATATGGCGCAAAATGACCAACAGCGGTTGATTGATCAGGTAGAGGGGCGCTGTA

CGAGGTAAAGCCCGATGCCAGCATTCCTGACGACGATACGGAGCTGCTGCGCGATTACGTAAAGAAGTTA

TTGAAGCATCCTCGTCAGTAAAAAGTTAATCTTTTCAACAGCTGTCATAAAGTTGTCACGGCCGAGACTT trpS.D.  XbaI
ATAGTCGCTTTGTTTTTATTTTTTAATGTATTTGTACGCAAGTTCACGTAAAAAGGGTATCTAGA
```

Fragments A, B, C and D were ligated in a four-part ligation and the ligation mixture used to transform *E. coli* 294. Transformants were identified by growth on LB plates containing ampicillin. Plasmid trpSTIITNF was isolated from a transformant colony. This plasmid was digested with XbaI and EcoRI to remove the trp promoter, then ligated to the 450 bp long EcoRI-XbaI fragment E containing the *E. coli* alkaline phosphatase promoter. The resulting plasmid is called pAPSTIITNF.

EXAMPLE 23

Expression and Processing of a Tumor Necrosis Factor Fusion with a Secretory Signal Sequence

*E. coli* NL106 was transfected with pAPSTIITNF and innoculated into 10 liters of a pH 7.0 medium having the following formula:

| Component | gms/L |
|---|---|
| (NH$_4$)$_2$SO$_4$ | 5.0 |
| K$_2$HPO$_4$ | 2.6 |
| NaH$_2$PO$_4$ | 1.3 |
| Na Citrate | 1.0 |
| KCl | 1.5 |
| NZ Amine AS | 5.0 |
| Yeast Extract | 2.0 |
| MgSO$_4$ | 1.2 |
| Glucose | 25.0 |
| Trace Element solution (Fe, Zn, Co, Mo, Cu, B and Mn ions) | 0.5 ml |
| Ampicillin | 20.0 mg |

The culture was conducted in the same fashion as described above in Example 19, except that an A$_{550}$ of 140 was reached. The culture at this point contained about 400 mg of tumor necrosis factor/liter, about 70–80 percent by weight of which was properly processed to the mature protein as estimated from electrophoresis gels. Approximately the same activity of tumor necrosis factor was recovered upon whole cell extraction by the method used in Example 19 as was recovered by osmotic shock of the cells.

I claim:

1. A method for preparing human tumor necrosis factor from an admixture with other proteins, comprising adsorbing the tumor necrosis factor from such admixture onto a silicate, and thereafter eluting the tumor necrosis factor from the silicate.

2. A method for preparing human tumor necrosis factor from an admixture with other proteins, comprising adsorbing the tumor necrosis factor from such admixture onto controlled pore glass, and thereafter eluting the tumor necrosis factor from the controlled pore glass.

3. The method of claim 2 wherein the tumor necrosis factor is eluted with ethylene glycol.

\* \* \* \* \*